US007585983B2

(12) United States Patent
Reuter et al.

(10) Patent No.: US 7,585,983 B2
(45) Date of Patent: Sep. 8, 2009

(54) ALKYLENEDIOXYTHIOPHENES AND POLY(ALKYLENEDIOXYTHIOPHENES) CONTAINING MESOGENIC GROUPS

(75) Inventors: Knud Reuter, Krefeld (DE); Alexander Karbach, Krefeld (DE); Helmut Ritter, Wuppertal (DE); Noelle Wrubbel, Düsseldorf (DE)

(73) Assignee: H.C. Starck, GmbH, Goslar (DE)

( * ) Notice: Subject to any disclaimer, the term of this patent is extended or adjusted under 35 U.S.C. 154(b) by 0 days.

(21) Appl. No.: 10/762,106

(22) Filed: Jan. 21, 2004

(65) Prior Publication Data

US 2004/0227128 A1 Nov. 18, 2004

(30) Foreign Application Priority Data

Jan. 21, 2003 (DE) ................ 103 02 086

(51) Int. Cl.
*C07D 495/04* (2006.01)
*C09K 19/34* (2006.01)
*C09K 19/32* (2006.01)
*C09K 19/38* (2006.01)
*C08G 75/06* (2006.01)
*H01B 1/12* (2006.01)

(52) U.S. Cl. ............... 549/50; 252/299.61; 252/299.62; 252/299.7; 252/500; 528/373; 528/377; 528/378; 528/380; 257/40

(58) Field of Classification Search ............ 252/299.01, 252/500, 299.61, 299.62, 299.7; 526/256, 526/377, 380; 528/373, 378, 379, 380, 425, 528/377; 549/50, 52, 57; 257/E51.029, 40

See application file for complete search history.

(56) References Cited

U.S. PATENT DOCUMENTS

| | | | | |
|---|---|---|---|---|
| 4,959,430 | A | 9/1990 | Jonas et al. | 526/257 |
| 4,987,042 | A | 1/1991 | Jonas et al. | 429/213 |
| 5,035,926 | A | 7/1991 | Jonas et al. | 427/393.1 |
| 5,111,327 | A | 5/1992 | Blohm et al. | 526/256 |
| 5,300,575 | A | 4/1994 | Jonas et al. | 525/186 |
| 6,130,339 | A | 10/2000 | Tan et al. | 549/50 |
| 6,756,473 | B2 * | 6/2004 | Reuter et al. | 528/377 |
| 6,852,830 | B2 * | 2/2005 | Groenendaal et al. | 528/373 |
| 2002/0165338 | A1 | 11/2002 | Martin et al. | 528/377 |
| 2003/0139505 | A1 | 7/2003 | Reuter et al. | 524/265 |
| 2003/0216540 | A1 | 11/2003 | Reuter | 528/380 |

FOREIGN PATENT DOCUMENTS

| | | |
|---|---|---|
| DE | 196 43 031 | 4/1998 |
| EP | 1 321 483 | 6/2003 |

OTHER PUBLICATIONS

Adv. Mater., 12, No. 7, (month unavailable) 2000, pp. 481-494 L. "Bert" Groenendaal et al, "Poly (3,4-ethylenedioxythiophene) and Its Derivatives: Past, Present, and Future".
Adv. Mater., 6, No. 2, (month unavailable) 1994, pp. 138-142, Christine Thobie-Gautier et al, "Electropolymerization of Thiophene Derivatized with a Mesogenic Substitutent".
Chem. Letters, (month unavailable) 2000, pp. 936-937, Masashi Kijima et al, "Synthesis of a Novel Ionic Liquid Crystalline Polythiophene Having Viologen Side Chain."
Journal of Material Science, 37, (month unavailable) 2002, pp. 1767-1775, A. Cirpan et al. "Synthesis and characterization of conducting copolymers of thiophene-3-yl acetic acid cholesteryl ester with pyrrole".
Macromolecules 24, (month unavailable) 1991, pp. 455-459, G. Daoust et al, "Structure-Property Relationships in Alkoxy-Substituted Polythiophenes".
Synthetic Metals, 124, (month unavailable) 2001, pp. 471-475, K. Krishnamoorthy et al, "Electrochromic polymer based on a rigid cyanobiphenyl substituted 3,4-ethylenedioxythiophene".
Synthetic Metals, 102, (month unavailable) 1999, pp. 1291, X.M. Dai et al, "Synthesis and properties of polythiophene derivatives with ferroelectric liquid crystalline substituents".
Krishnamoorthy, K. et al: "Dendronized electrochromic polymer based on poly(3,4-ethylenedioxy-thiophene)" Polymers, 43(24), 6465-6470 Coden: Polmag; ISSN: 0032-3861, 2002, XP000438533.
Kros, Alexander et al: "Poly(3,4-ethylenedioxythiophene)-based copolymers for biosensor applications" Journal of Polymer Science, Part A: Polymer Chemistry, 40(6), 738-747 Coden: JPACEC; ISSN: 0887-624X, 2002, XP002244145.
Perepichka, Igor F. et al: Hydrophilic Oligo(oxyethylen)-Derivatized Poly(3,4-ethylenedioxy-thiophenes): Cation-Responsive Optoelectroelectrochemical Properties and Solid-State Chromism: Chemistry of Materials, 14(1), 449-457 Coden: Cmatex; ISSN: 0897-4756, 2002, XP001182404.
Besbes, Mohamed et al: "Rapid and efficient post-polymerization functionalization of poly(3,4-ethylenedioxythiophene) (PEDOT) derivatives on an electrode surface" Advanced Materials (Weinheim, Germany), 13(16), 1239-1252 Coden: Advmew: ISSN: 0935-9648, 2001, XP001130234.

* cited by examiner

*Primary Examiner*—Shean C Wu
(74) *Attorney, Agent, or Firm*—Connolly Bove Lodge & Hutz LLP

(57) ABSTRACT

The invention relates to new 3,4-alkylenedioxythiophenes which are substituted with mesogenic groups, if desired via a bridging group, and their polymeric derivatives (poly-(3,4-alkylenedioxythiophenes)).

19 Claims, 1 Drawing Sheet

ALKYLENEDIOXYTHIOPHENES AND POLY(ALKYLENEDIOXYTHIOPHENES) CONTAINING MESOGENIC GROUPS

BACKGROUND OF THE INVENTION

1. Field of the Invention

The invention relates to new 3,4-alkylenedioxythiophenes which are substituted with mesogenic groups and their polymeric derivatives (poly-(3,4-alkylenedioxythiophenes)).

2. Brief Description of the Prior Art

It is generally known that π-conjugated polymers display interesting (nonlinear) optical properties because of the considerable delocalization of the π electrons along the main chain. After oxidation or reduction, they are good electric conductors and in the uncharged form they possess good semiconducting properties. They are, therefore, of interest for use in fields such as data storage, optical signal processing, suppression of electromagnetic interference (EMI) and solar energy conversion, and also in rechargeable batteries, light-emitting diodes, field effect transistors, printed circuits, sensors and antistatic materials.

Poly(3,4-alkylenedioxythiophenes) and their derivatives, in particular poly(3,4-ethylenedioxythiophene) and its derivatives are of particular interest, owing to their high conductivities, especially in the cationic (oxidized) form, and their good processability (EP-A 339 340 and L. Groenendaal, F. Jonas, D. Freitag, H. Pielartzik & J. R. Reynolds, Adv. Mater. 12, (2000) pp. 481-494).

Despite these good properties of poly(3,4-ethylenedioxythiophene), there is a need for further improvement to meet the requirements of conductive and semiconducting materials. The conductive or semiconducting materials have to meet very demanding requirements, in particular the ordering requirement, for use in, for example, molecular electronics, solar technology or semiconductor technology.

Hitherto, the prior art has not disclosed means of influencing a high degree of preorientation of the poly(3,4-ethylenedioxythiophene) in a solid phase, since conductive or semiconducting polymers are processed mainly from the liquid phase, e.g. solution, suspension or dispersion.

However, it is envisaged that such preorientation could be achieved by self-organization of the monomers during the polymerization by creating structural prerequisites for short-range order.

In this regard, the prior art discloses a number of attempts to prepare π-conjugated polymers bearing mesogenic groups as substituents, i.e. groups which promote the formation of mesogenic phases. Described hereinbelow are the prior art products and processes and their shortcomings.

Attempts to prepare thiophenes containing mesogenic substituents or their polymeric downstream products have also been described in a few publications. J. Roncali et al. (Adv. Mater. 1994, 6(2), pp. 138-142) describe the synthesis of 4-cyano-4'-(8-(3-thienyl)oxy)biphenyl, its liquid-crystalline behavior and electro-chemical polymerization thereof to form the corresponding polythiophene. Its electrical conductivity is said to be from 0.01 to 0.1 S/cm. In Synthetic Metals 1999, 102, p. 1291, Akagi et al. report liquid-crystalline polythiophenes bearing chiral mesogenic groups as substituents without giving any further information on the electrical properties. Kijima et al. report a cationic, viologen-substituted liquid-crystalline polythiophene and describe its redox behaviour and the electric conductivity of $3.5 \times 10^{-3}$ S/cm in the $I_2$-doped state, but this is extremely low with a view to the abovementioned applications (Chem. Letters 2000, pp. 936-937). Yagci et al. describe the preparation of the liquid-crystalline cholesteryl 3-thiopheneacetate which was oxidatively polymerized by chemical and electrochemical means to give the polythiophene having a conductivity of 0.05 S/cm (J. Mater. Sci. 2002, 37, pp. 1767-1775).

All the polythiophenes described in the abovementioned references have two disadvantages caused by their structure. Firstly, the substitution of the thiophene unit exclusively in position 3 leads to secondary reactions in the polymerization, since a reactive H is present as substituent in the 4 position. In particular α,β'-coupling can lead to structural defects, i.e. interruption of the conjugation in the polymer and shortened conjugation lengths, resulting in unsatisfactory conductivities. Secondly, according to the above mentioned publications, the thiophenes which are C-substituted exclusively in the 3 position always exhibit only moderate stabilities of the highly conductive cationic state of the polythiophenes (e.g. after iodine doping). These disadvantageous are well known for analogous polythiophenes which are not liquid-crystalline, cf., for example, Leclerc et al., Macromolecules 1991, 24, pp. 455-459.

In Synthetic Metals 2001, 124, pp. 471-475 Kumar et al. described a 3,4-ethylenedioxythiophene having bulky substituents and its electrochemical polymerization to form the correspondingly substituted poly(3,4-ethylenedioxythiophene), as well as studies on these polymers with a view to improved transparency. Although the bulky substituent can be regarded as a potential mesogenic group, no indications were given of liquid-crystalline behaviour of the monomer or polymer and no studies on this subject were reported.

There is, therefore, a continuing need for 3,4-alkylenedioxythiophenes which bear mesogenic groups as substituents.

SUMMARY OF THE INVENTION

The present invention accordingly provides 3,4-alkylenedioxythiophenes, characterized in that they are substituted by a mesogenic group M, if desired via a bridging group B, with the exception of the 3,4-alkylenedioxythiophene of the formula (i)

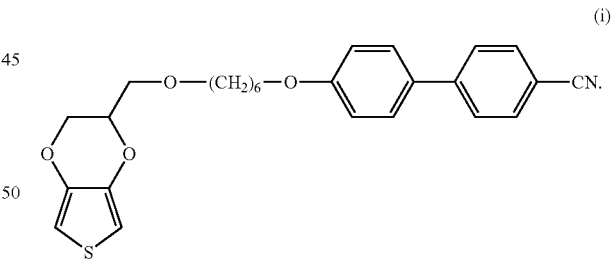

The term "mesogenic group" encompasses all groups or substances which, in a particular temperature range, are capable of forming mesophases, i.e. phases having a higher degree of order than isotropic liquids but a lower degree of order than crystals. Such phases (still) display the optical anisotropy of crystals and (also) the mobility of completely isotropic liquids. Mesophases are also described as liquid-crystalline phases or anisotropic liquids.

For the purposes of the invention, the mesogenic group can be a group which is capable of forming smectic, nematic or cholesteric liquid-crystalline phases. They can thus be rod-shaped, disc-shaped (discotic) or cholesteric mesogenic groups.

DETAILED DESCRIPTION OF THE INVENTION

Figure 1:
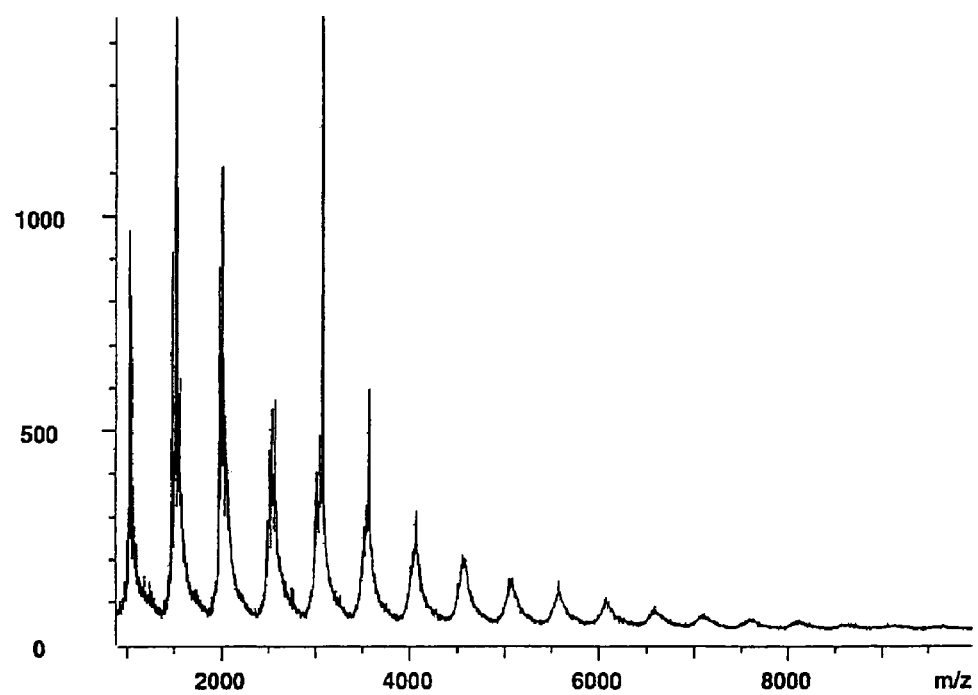
FIG. 1 is a the MALDI-TOF-MS characterization of uncharged polythiophene prepared from thiophenes (I-a5) and (I-b5) prepared in Example 6.

The invention is described more fully hereunder with particularity but without limitation to its preferred embodiments. Preferred 3,4-alkylenedioxythiophenes according to the present invention are 3,4-alkylenedioxythiophenes of the formula (I),

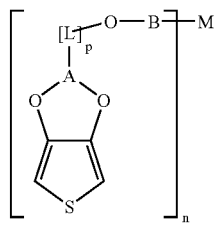
(I)

where
A is a $C_1$-$C_5$-alkylene radical which is substituted at any point by a linker L and may bear further substituents,
L is a methylene group,
p is 0 or an integer from 1 to 6, preferably 0 or 1,
M is an n-functional mesogenic group,
n is an integer from 1 to 8 and
B is a bridging group of the formula (B)

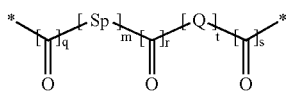
(B)

where
q is 0 or 1,
r, s are each 0 or 1, with the proviso that when r is 1, s is 0 and vice versa or both may be 0,
t is 0 or 1,
Sp is a spacer selected from among substituted and unsubstituted linear or cyclic $C_1$-$C_{20}$-alkylene groups, $C_5$-$C_{20}$-arylene groups, preferably $C_6$-$C_{20}$-arylene groups, $C_2$-$C_{20}$-heteroarylene groups in which from one to three heteroatoms selected from among N, O and S can additionally be present in the heteroaromatic ring or ring system, $C_6$-$C_{20}$-aralkylene groups, preferably $C_7$-$C_{20}$-aralkylene groups, and $C_2$-$C_{200}$-, preferably $C_2$-$C_{80}$-oligoether and -polyether groups,
m is 0 or 1,
Q is O, S or NH.

Both pure 3,4-alkylenedioxythiophenes of the formula (I) and any mixtures of these are encompassed by the invention.

Particular preference is given to 3,4-alkylenedioxythiophenes or mixtures of 3,4-alkylenedioxythiophenes which have a structure of the formula (I-a) and/or (I-b),

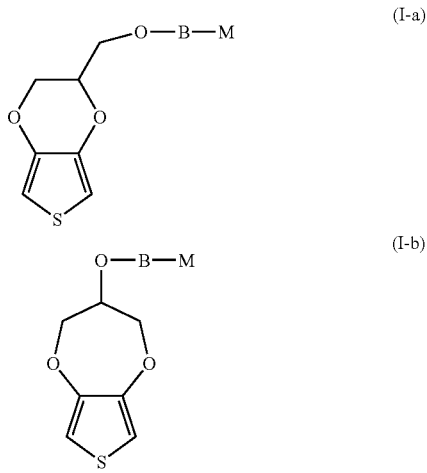

where
B and M are as defined above for the formula (I) and/or in the following.

If the thiophenes in question are mixtures of 3,4-alkylenedioxythiophenes of the formulae (I-a) and (I-b), it is possible according to the invention for 3,4-alkylenedioxythiophenes of the formulae (I-a) and (I-b) to be present in this mixture in any molar ratio. Preference is given to 3,4-alkylenedioxythiophenes of the formula (I-a) being present in an amount of from 65 to 99.9%, particularly preferably an amount of from 75 to 99.5%, based on the total molar amount of thiophenes, and the 3,4-allkylenedioxythiophenes of the formula (I-b) being present in an amount of from 0.1 to 35%, particularly preferably an amount of from 0.5 to 25%, based on the total molar amount of thiophenes, with the proviso that the sum of the two amounts is 100%.

For the purposes of the invention, preference is given to
M being an n-functional group of the formula (II-a) or (II-b),

(II-a)

(II-b)

where
$X^1$, $X^2$, $X^3$ are substituted or unsubstituted structures selected independently from among

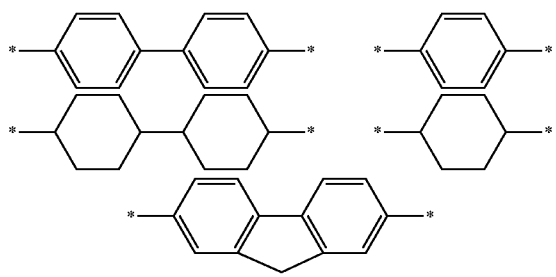

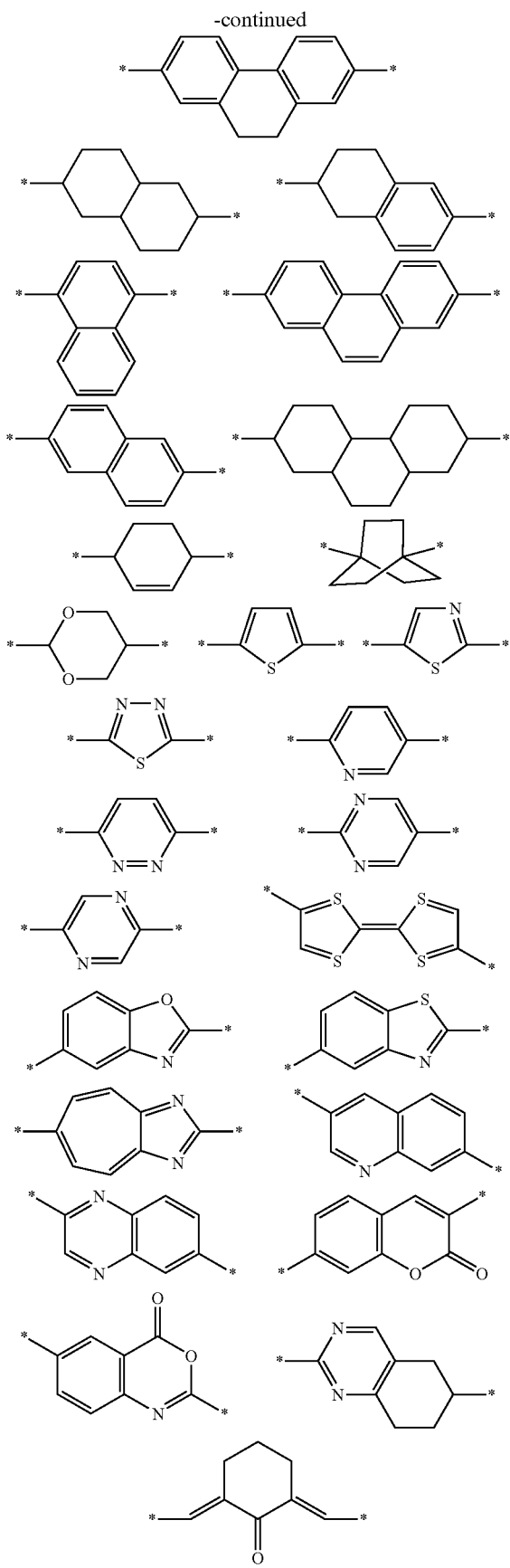

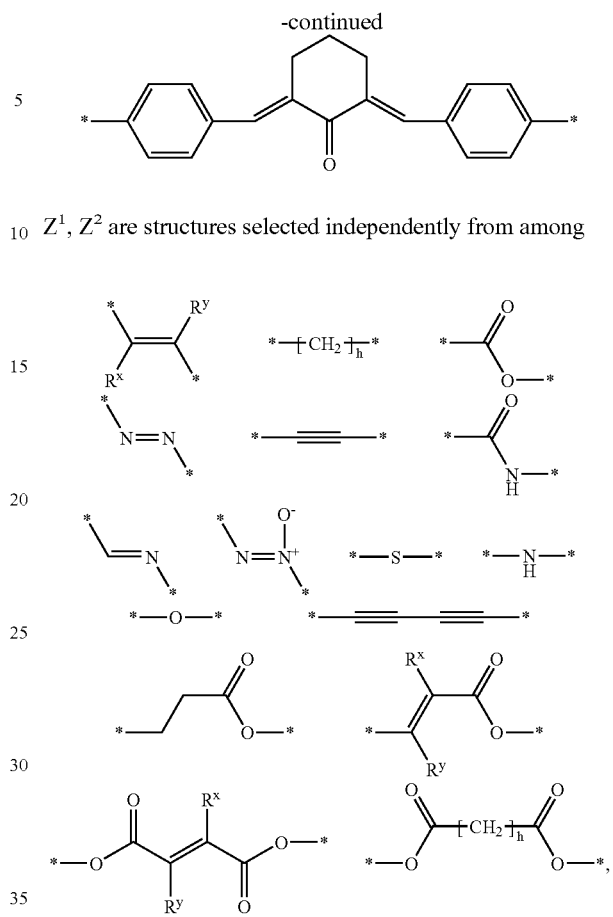

$Z^1$, $Z^2$ are structures selected independently from among

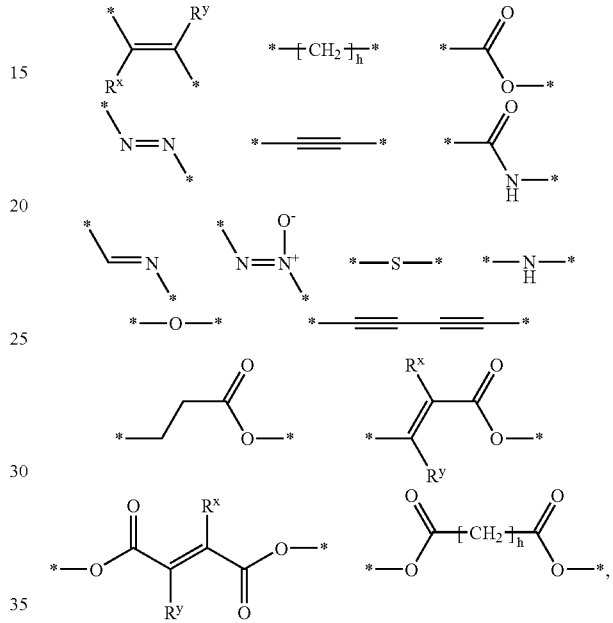

where
$R^x$ and $R^y$ are each, independently of one another, H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, $NO_2$, a carboxyl group or a hydroxy group,
h is an integer from 1 to 10,
w is an integer from 1 to 5, preferably from 1 to 3,
x, y, z are each, independently of one another, 0 or 1, and
n is 1 or 2, where
when n is 1, the group of the formula (II-a) or (II-b) bears a terminal group F at the linkage points indicated by *, where
F is H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, a nitro ($NO_2$) group, a carboxyl group, a sulphonic acid group or sulphonate group or a hydroxy group.

In a preferred embodiment of the invention in which M is an n-functional group of the formula (II-a), w is an integer from 2 to 5 and $X^1$, n and F can be as defined above.

A special case exists when w in the formula (II-a) is 1. In this case, $X^1$ can bear a terminal group F, for example a carboxyl group —COOH or an acrylic acid radical, e.g.

—CH=CH—COOH, at one of the linkage points denoted by *, so that a mesogenic group is formed by dimerization.

Therefore, in other preferred embodiments of the invention, in which M is an n-functional group of the formula (II-a), w is 1, n is 1 and F is a carboxyl group, —COOH or an acrylic acid radical, —CH=CH—COOH, particularly when $X^1$ is a monocyclic structure selected from among those mentioned above for $X^1$.

Examples of substituents which may be present on $X^1$, $X^2$ and $X^3$ are linear, branched or cyclic $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, radicals of aliphatic $C_1$-$C_{22}$-alkanecarboxylic acids or of acrylic acid, halogens, pseudohalogens, $NO_2$, a carboxyl group and a hydroxy group.

In preferred embodiments of the present invention, $X^1$, $X^2$ and $X^3$ are unsubstituted.

Preference is also given, for the purposes of the invention, to

M being an n-functional group selected from among the formulae (II-c-1) to (II-c-6),

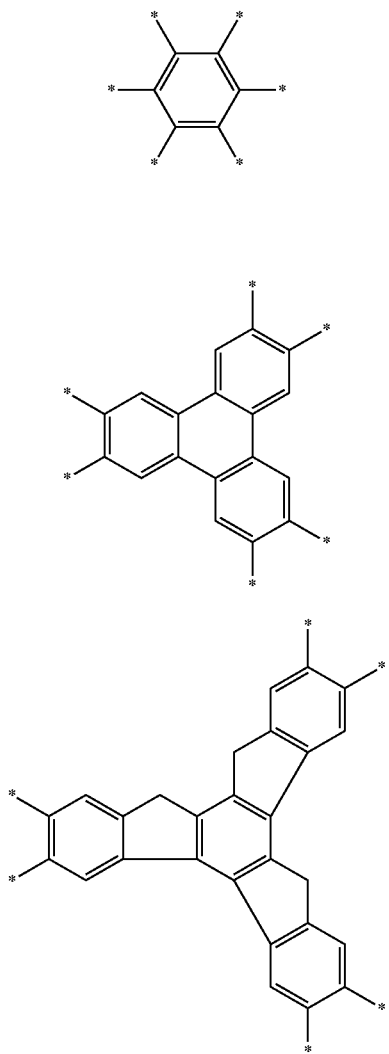

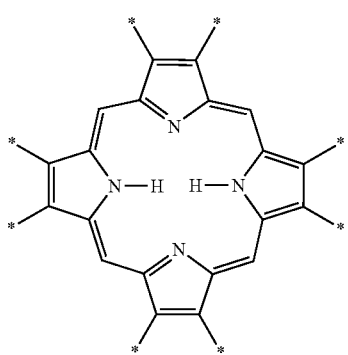

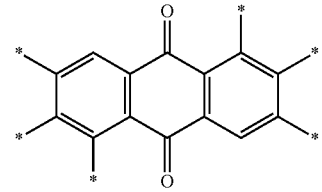

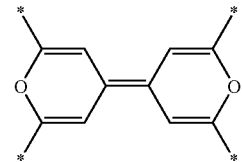

where
n is an integer from 1 to 8 and,
when n is an integer below 8, the group selected from among the formulae (II-c-1) to (II-c-6) bears a terminal group F on the remaining 8-n linkage points denoted by *, where
F is H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, $NO_2$, a carboxyl group, a sulphonic acid group or sulphonate group or a hydroxy group.

Preference is likewise given, for the purposes of the invention, to

M being a steroid radical or a derivative of a steroid radical, particularly preferably a cholesteryl radical or a derivative of the cholesteryl radical of the formula (III-a),

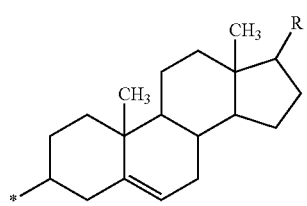

where
R is H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, $NO_2$, a carboxyl group, a sulphonic acid group or sulphonate group or a hydroxy group.

The steroid radicals or derivatives thereof are preferably bound via the C(3) atom of the A ring in the basic gonane skeleton

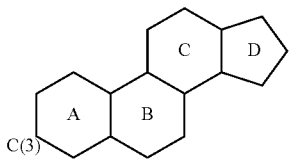

Steroid radicals or derivatives of steroid radicals can be, apart from the cholesteryl radical and its derivatives, radicals of, for example, the formulae (III-b) to (III-e),

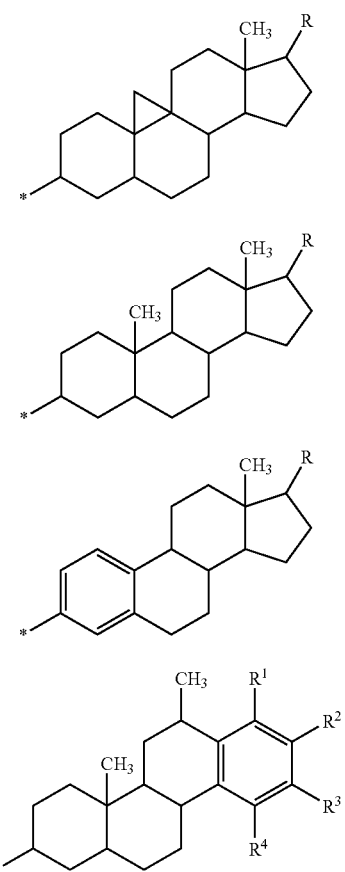

where R, $R^1$, $R^2$, $R^3$ and $R^4$ can, independently of one another, be as defined above for R. However, this listing is purely by way of example and is not intended to be comprehensive.

In the formulae (III-a) to (III-e), the configurations on the individual stereocenters are not drawn in. The present invention encompasses in principle all known stereoisomers and mixtures thereof, but preference is given to the naturally occurring stereoisomers and mixtures thereof.

The 3,4-alkylenedioxythiophenes of the invention can have at least one chiral carbon atom in the alkylene radical A.

In these cases, the term "3,4-alkylenedioxythiophenes of the invention" encompasses the pure stereoisomers, enantiomers or diastereomers and any mixtures of these.

The presence of chiral compounds in liquid-crystalline phases enables a helix-like superstructure to be formed. Such phases can have ferroelectric properties.

The 3,4-alkylenedioxythiophenes of the invention can be prepared from hydroxy compounds of the formula (V),

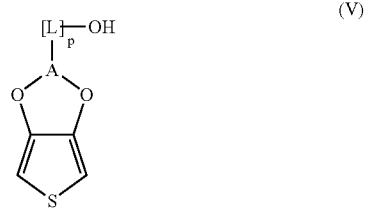

where A, L and p can be as defined above, by reaction with appropriate reactants using known methods depending on the meanings of B and M. In principle, all processes using all reactants which can react with the hydroxy group in formula (V) to attach an ether group (—O—) or oxycarbonyl group (—O—CO—) are suitable. The known processes can, depending on the meaning of B, be, for example, esterification or etherification reactions, but other types of reaction are also possible. As functional group which is reactive towards the hydroxy group in formula (V), the reactants can contain, for example, a carboxyl group or derivative thereof, an aldehyde group, halogen or other group. Examples which may be mentioned here are cholesteryl chloroformate, [(4'-cyano-1,1'-biphenyl-4-yl)oxy]carboxylic acids or [(4'-bromo-1,1'-biphenyl-4-yl)oxy]carboxylic acids. Suitable reactants which are not commercially available can be prepared prior to attachment to the compounds of the formula (V) from stating materials containing the group B or M or from starting materials which form the groups B and M only after they have been attached. It is also possible to attach B and M stepwise by firstly reacting the hydroxy compounds of the formula (V) with a bifunctional reactant which contains, for example, the group B and then reacting the intermediate, either after isolation or in situ, with a further reactant which contains, for example, the group M to form the 3,4-alkylenedioxythiophenes of the invention. Such processes are likewise known to those skilled in the art. Examples of bifunctional reactants are α,ω-dihalo compounds such as 1,6-dibromohexane; examples of reactants containing the group M are 4-(4-alkoxyphenyl)phenol and 4-(4-bromophenyl) phenol. The hydroxy compounds of the formula (V) can be prepared from alkanetriols and 3,4-dialkoxythiophenes in an acid-catalysed transetherification reaction. 3,4-dialkoxythiophenes which are suitable for this purpose are, in particular, those having short-chain n-alkoxy groups, preferably methoxy, ethoxy and n-propoxy groups. This procedure is described in principle in Adv. Mater. 11 (1999), pp. 1379-1381. The preferred starting compounds EDT-methanol and hydroxy-PDT can also be prepared in admixture as described in U.S. Pat. No. 5,111,327. However, it is also possible to use the pure compounds which are obtainable, for example, by means of a chromatographic separation as described in U.S. Pat. No. 5,111,327. EDT-methanol can also be prepared directly in pure form by the method of Reynolds et al., Polym. Prepr. (Am. Chem. Soc., Div. Polym. Chem.) 38(2), (1997), 320, using 2,3-dibrompropyl acetate.

The 3,4-alkylenedioxythiophenes are very suitable for the preparation of polythiophenes.

For this reason, the present invention likewise provides for the use of the 3,4-alkylenedioxythiophenes of the invention or mixtures thereof for preparing polythiophenes.

The invention further provides polythiophenes, characterized in that they comprise recurring units of the formula (IV),

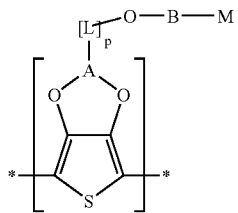

(IV)

where
A, L, p, M and B are as defined above, with the exception of polythiophenes consisting of recurring units of the formula (ii)

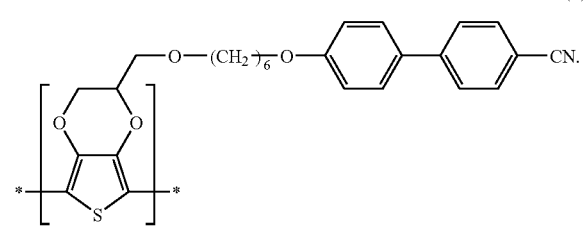

(ii)

For the purposes of the invention, these can be polythiophenes comprising identical or different recurring units of the formula (IV); in the case of different recurring units of the formula (IV), the polythiophenes are copolymers. Depending on the arrangement of the various recurring units of the formula (IV), these can be random, alternating, gradated or block copolymers.

Preferred polythiophenes of the invention are characterized in that they comprise recurring units of the formulae (IV-a) and/or (IV-b),

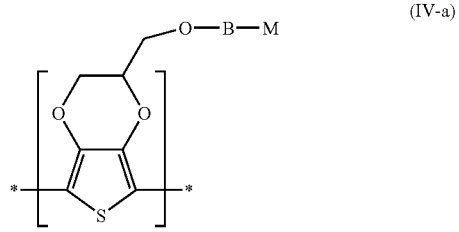

(IV-a)

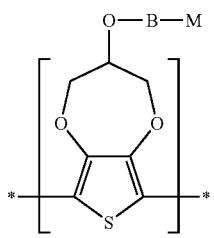

(IV-b)

where
M and B are as defined above.

In these preferred polythiophenes according to the invention, the recurring units of the formulae (IV-a) and (IV-b) can, for the purposes of the invention, be present in any molar ratio. Particular preference is given to polythiophenes according to the invention which comprise recurring units of the formula (IV-a) in an amount of from 65 to 99.9%, very particularly preferably an amount of from 75 to 99.5%, based on the total molar amount of recurring units, and recurring units of the formula (IV-b) in an amount of from 0.1 to 35%, very particularly preferably an amount of from 0.1 to 25%, based on the total molar amount of recurring units, with the proviso that the sum of the two amounts is 100%.

For the purposes of the invention, the term polythiophenes preferably encompasses all compounds comprising at least 2 and not more than 200, preferably at least 2 and not more than 50, recurring units of the formula (IV).

The polythiophenes of the invention are preferably uncharged and semiconducting or cationic and electrically conductive. In the case of cationic polythiophenes, the positive charges of the polythiophene polycations are not shown in the formulae (IV), (IV-a), (IV-b), since their precise number and their position cannot be established precisely. However, the number of positive charges is at least 1 and not more than the total number of all recurring units in the polythiophene.

To compensate the positive charge, the cationic form of the polythiophenes contains anions, preferably polyanions, as counterions.

Polyanions present are preferably the anions of polymeric carboxylic acids such as polyacrylic acids, polymethacrylic acid or polymaleic acids and polymeric sulphonic acids such as polystyrenesulphonic acids and polyvinylsulphonic acids. These polycarboxylic and polysulphonic acids can also be copolymers of vinylcarboxylic and vinylsulphonic acids with other polymerizable monomers, e.g. acrylic esters and styrene.

The anion of polystyrenesulphonic acid is particularly preferred as counterion.

The molecular weight of the polyacids from which the polyanions are derived is preferably from 1000 to 2000000, particularly preferably from 2 000 to 500 000. The polyacids or their alkali metal salts are commercially available, e.g. polystyrenesulphonic acids and polyacrylic acids.

The polythiophenes comprising recurring units of the formula (IV) can be prepared by chemical or electrochemical oxidative polymerization of the 3,4-alkylenedioxythiophenes of the invention.

Accordingly, the present invention further provides a process for preparing polythiophenes comprising recurring units of the formula (IV), with the exception of polythiophenes consisting of recurring units of the formula (ii), characterized in that compounds of the formula (I),

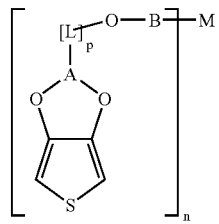 (I)

where
A, L, p, M and B are as defined above, are oxidatively polymerized by electrochemical means.

The electrochemical oxidative polymerization of the 3,4-alkylenedioxythiophenes of the invention can be carried out at temperatures of from −78° C. to the boiling point of the solvent used or the 3,4-alkylenedioxythiophene according to the invention. Preference is given to carrying out the electrolysis at temperatures of from −20° C. to 60° C.

The reaction times depend on the monomer used, the electrolyte used, the electrolysis temperature selected and the current density employed and are in the range from 1 minute to 24 hours.

If the 3,4-alkylenedioxythiophenes according to the invention are liquid under the electrolysis conditions, the electropolymerization can be carried out in the presence or absence of solvents which are inert under the electrolysis conditions. The electropolymerization of 3,4-alkylenedioxythiophenes according to the invention which are solid under the electrolysis conditions is carried out in the presence of solvents which are inert under the electrolysis conditions. In certain cases it can be advantageous to use solvent mixtures and/or to add solubilizers (detergents) to the solvents.

Examples of solvents which are inert under the electrolysis conditions are: water; alcohols such as methanol and ethanol; ketones such as acetophenone; halogenated hydrocarbons such as methylene chloride, chloroform, carbon tetrachloride and fluorinated hydrocarbons; esters such as ethyl acetate and butyl acetate; carboxylic esters such as propylene carbonate; aromatic hydrocarbons such as benzene, toluene, xylene; aliphatic hydrocarbons such as pentane, hexane, heptane and cyclohexane; nitriles such as acetonitrile and benzonitrile; sulphoxides such as dimethyl sulphoxides; sulphones such as dimethyl sulphone, phenyl methyl sulphone and sulpholane; liquid aliphatic amides such as methylacetamide, dimethylacetamide, dimethylformamide, pyrrolidone, N-methylpyrrolidone, N-methylcaprolactam; aliphatic, mixed aliphatic-aromatic and cycloc ethers such as diethyl ether, tetrahydrofuran and anisole; liquid ureas such as tetramethylurea or N,N-dimethylimidazolidinone. The polymerization can also be carried out from a lyotropic liquid-crystalline phase.

To carry out the electropolymerization, the novel 3,4-alkylenedioxythiophenes or their solutions are admixed with electrolyte additives. Electrolyte additives used are preferably free acids or customary electrolyte salts which have a significant solubility in the solvents used. Electrolyte additives which have been found to be useful are, for example: free acids such as p-toluenesulphonic acid, methanesulphonic acid, also salts comprising alkanesulphonate, aromatic sulphonate, tetrafluoroborate, hexafluorophosphate, perchlorate, hexafluoroantimonate, hexafluoroarsenate and hexachloroantimonate anions and alkali metal, alkaline earth metal or alkylated or unalkylated ammonium, phosphonium, sulphonium and oxonium cations. The abovementioned polymeric counterions can, if appropriate, also be added to the electrolysis solution or the 3,4-alkylenedioxythiophenes of the invention as electrolyte additives or electrolyte salts in the electrochemical polymerization.

The concentrations of the 3,4-alkylenedioxythiophenes according to the invention can be in the range from 0.01 to 100% by weight (100% by weight only in the case of a liquid thiophene); the concentrations are preferably from 0.1 to 5% by weight.

The electropolymerization can be carried out batchwise or continuously.

The current densities for the electropolymerization can vary within wide limits; it is usual to employ current densities of from 0.0001 to 100 mA/cm$^2$, preferably from 0.01 to 40 mA/cm$^2$. At these current densities, voltages of from about 0.1 to 50 V are established.

The present invention likewise provides a process for preparing polythiophenes comprising recurring units of the formula (IV), characterized in that compounds of the formula (I),

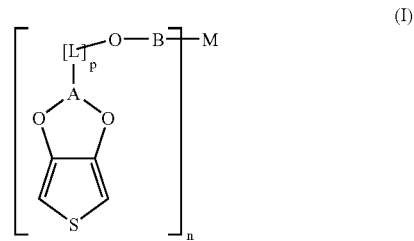 (I)

where
A, L, p, M and B are as defined above, are oxidatively polymerized by chemical means.

The oxidative chemical polymerization of the 3,4-alkylenedioxythiophenes according to the invention is generally carried out at temperatures of from −10° C. to 250° C., preferably temperatures of from 20° C. to 200° C., depending on the oxidant used and the desired reaction time.

Suitable solvents for the 3,4-alkylenedioxythiophenes of the invention and/or the oxidants are, in particular, the following organic solvents which are inert under the reaction conditions: aliphatic alcohols such as methanol, ethanol, i-propanol and butanol; aliphatic ketones such as acetone and methyl ethyl ketone; aliphatic carboxylic esters such as ethyl acetate and butyl acetate; aromatic hydrocarbons such as toluene and xylene; aliphatic hydrocarbons such as hexane, heptane and cyclohexane; chlorinated hydrocarbons such as dichloromethane, chloroform and dichloroethane; aliphatic nitriles such as acetonitrile, aliphatic sulphoxides and sulphones, e.g. dimethyl sulphoxide and sulpholane; aliphatic carboxamides such as methylacetamide and dimethylformamide; aliphatic, araliphatic and cyclic ethers such as diethyl ether, tetrahydrofuran and anisole. It is also possible to use water or mixtures of water with the abovementioned organic solvents as solvent. The polymerization can also be carried out from the lyotropic liquid-crystalline phase.

Oxidants used are the oxidants which are known to those skilled in the art as being suitable for the oxidative polymerization of thiophenes; these are described, for example, in G. Koβmehl, Makromol. Chem., Macromol. Symp. 4, 45-64 (1986). For practical reasons, preference is given to inexpensive and easy-to-handle oxidants such as iron(III) salts of inorganic acids, for example $FeCl_3$, $Fe(ClO_4)_3$ or $Fe_2(SO_4)_3$, and the iron(III) salts of organic acids and inorganic acids bearing organic radicals, also $H_2O_2$, $K_2Cr_2O_7$, alkali metal and ammonium peroxidedisulphates, alkali metal perborates, potassium permanganate, copper salts such as copper tetrafluoroborate or cerium(IV) salts or $CeO_2$. The presence of catalytic amounts of metal ions, e.g. iron, cobalt, nickel, copper, molybdenum or vanadium ions, may be helpful.

The oxidative polymerization of the 3,4-alkylenedioxythiophenes of the invention and possible subsequent oxidation of the poly-3,4-alkylenedioxythiophenes theoretically requires about 2.25 equivalents of oxidant per mole of thiophene (cf., for example, J. Polym. Sc. Part A Polymer Chemistry Vol. 26, p. 1287 (1988)). However, smaller or larger numbers of equivalents of oxidant can also be used. For the purposes of the invention, preference is given to using one equivalent or more, particularly preferably 2 equivalents or more, of oxidant per mole of thiophene.

Examples of iron(III) salts of inorganic acids having organic radicals are the iron(III) salts of sulphuric monoesters of $C_1$-$C_{20}$-alkanols, e.g. the Fe(III) salt of lauryl sulphate.

Examples of iron(III) salts of organic acids are: the Fe(III) salts of $C_1$-$C_{20}$-alkanesulphonic acids, e.g. of methanesulphonic or dodecanesulphonic acid, aliphatic $C_1$-$C_{20}$-carboxylic acids such as 2-ethylhexylcarboxylic acid, aliphatic perfluorocarboxylic acids such as trifluoroacetic acid and perfluorooctanoic acid, aliphatic dicarboxylic acids such as oxalic acid and especially of aromatic sulphonic acids which may be substituted by $C_1$-$C_{20}$-alkyl groups, e.g. benzenesulphonic acid, p-toluenesulphonic acid and dodecylbenzenesulphonic acid, and cycloalkanesulphonic acids such as camphorsulphonic acid.

It is also possible to use mixtures of these Fe(III) salts of organic acids.

Furthermore, in the case of cationic polythiophenes, any anions of the oxidant used can serve as counterions to the polythiophenes according to the invention, so that in the case of chemical oxidative polymerization, addition of additional counterions is not absolutely necessary.

In preferred embodiments of the process of the invention, the compounds of the formula (I) or mixtures thereof which are used are compounds having a structure corresponding to the formulae (I-a) and/or (I-b),

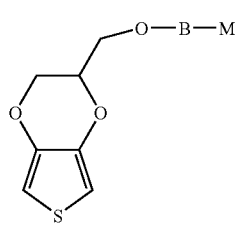

(I-a)

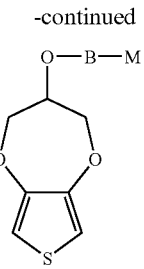

(I-b)

where
B and M are as defined above.

In particularly preferred embodiments of the process of the invention, a mixture of 3,4-alkylenedioxythiophenes of the formulae (I-a) and (I-b), where B and M are as defined above, is used.

For the purposes of the invention, the 3,4-alkylenedioxythiophenes of the formulae (I-a) and (I-b) can be present in these mixtures in any molar ratio. The 3,4-alkylenedioxythiophenes of the formula (I-a) are preferably present in an amount of from 65 to 99.9%, particularly preferably an amount of from 75 to 99.5%, based on the total molar amount of thiophenes, and the 3,4-alkylenedioxythiophenes of the formula (I-b) are preferably present in an amount of from 0.1 to 35%, particularly preferably an amount of from 0.1 to 25%, based on the total molar amount of thiophenes, with the proviso that the sum of both amounts is 100%. The molar proportions of the 3,4-alkylenedioxythiophenes of the formulae (I-a) and (I-b) may correspond to the molar proportions of the recurring units of the formulae (VI-a) and (VI-b) in the resulting polythiophenes according to the invention, but can also be different from these.

For the purposes of the invention, $C_1$-$C_5$-alkylene radicals can be methylene, ethylene, n-propylene, n-butylene or n-pentylene; linear or cyclic $C_1$-$C_{20}$-alkylene radicals can be, in addition to the radicals just mentioned, n-hexylene, n-heptylene, n-octylene, n-nonylene, n-decylene, n-undecylene, n-dodecylene, n-tridecylene or n-tetradecylene, n-hexadecylene, n-octadecylene or n-eicosylene, cyclopentylene, cyclohexylene, cycloheptylene, cyclooctylene, cyclononylene or cyclodecylene. Linear, branched or cyclic $C_1$-$C_{22}$-alkyl radicals can for the purposes of the present invention be, for example, methyl, ethyl, n-propyl or isopropyl, n-butyl, isobutyl, sec-butyl or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl or n-tetradecyl, n-hexadecyl, n-octadecyl or n-eicosyl, n-docosyl, cyclopentyl, cyclohexyl, cycloheptyl, cyclooctyl, cyclononyl or cyclodecyl, where cyclic alkyl radicals are at least $C_5$-cycloalkyl radicals. $C_5$-$C_{20}$-arylene radicals can be, for example, phenylene, naphthylene, biphenylene, fluorenylene, indenylene, cyclopentadienylene or anthracenylene and $C_6$-$C_{20}$-aralkylene radicals can be, for example, o-, m-, p-tolylene, benzylene, 2,3-, 2,4-, 2,5-, 2,6-, 3,4-, 3,5-xylylene or mesitylene. $C_2$-$C_{20}$-heteroarylene radicals can be based on all heteroaromatic ring systems which have, in addition to the carbon atoms, from one to three heteroatoms selected from among N, O and S in the heteroaromatic ring or ring systems, for example pyrrol, thiophene, furan, pyridine, indole, carbazole, pyrazole, imidazole or thiazole. For the purposes of the invention, $C_2$-$C_{200}$-oligoether or -polyether groups can be groups having from one to 50 O atoms in the oligoether or polyether chain, and $C_2$-$C_{80}$-oligoether or -polyether groups can be groups having from one to 20O atoms, where the smallest oligoether group having two carbon atoms is a dimethylene ether group (—$CH_2$—O—$CH_2$—). $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy and radicals of aliphatic $C_1$-$C_{22}$-alkanecarboxylic acids can be derived from the abovementioned $C_1$-$C_{22}$-alkyl radicals by appropriate replacement of an H atom by the functional group. Halogens can be, for example, fluorine, chlorine, bromine and iodine; pseudohalogen can be, for example, a cyano, thiocyano, isocyano or isothiocyano group. The above listing serves merely to illustrate the invention by way of example and is not intended to be exhaustive.

Substituents which may be present on, for example, $C_1$-$C_{22}$-alkyl are, for example, halogen, pseudohalogen or keto, aldehyde, amino, hydroxy, nitro, thiohydroxy (mercapto), carboxyl, carboxylate, sulphonic acid or sulphonate groups.

If the principle of mesogenic groups is, as in the case of the present invention, combined with polymers, liquid-crystalline polymers can be obtained. However, depending on the degree of molecular order, it is also possible for polymers having improved properties, e.g. higher conductivity, but no liquid-crystalline properties to be formed.

The polythiophenes of the present invention are suitable as constituents of electrical or electronic components, light-emitting components, in particular organic electrical or electronic components or light-emitting components, e.g. lighting elements, photocells or organic transistors. Furthermore, they can be used for antistatic coatings, e.g. for treatment of plastic films for packaging electronic components and for clean room packaging, for making cathode ray tubes antistatic or for making photographic films antistatic, in optoelectronics, e.g. as transparent heating, as transparent electrodes, as circuit boards or for electrochromic windows, or in solar energy technology.

The present invention therefore likewise provides for the use of the polythiophenes of the invention as constituents in electrical or electronic components, light-emitting components, for antistatic coatings, in optoelectronics or in solar energy technology.

The conductivity of, for example, constituents in electrical or electronic components, light-emitting components or antistatic coatings comprising the polythiophenes of the invention can be increased further by means of heat treatment. This can involve intermediate formation of liquid-crystalline phases. The heat treatment is preferably carried out at temperatures of from 80° C. to 300° C., particularly preferably from 100° C. to 250° C., for a period of from 15 minutes to 6 hours, particularly preferably from 30 minutes to 4 hours. In the case of polythiophenes according to the invention which have been prepared by chemical oxidative polymerization, the heat treatment is preferably carried out after excess reactants, for example oxidant or excess monomer, have been washed out by means of a suitable solvent, preferably water or alcohols.

The polythiophenes of the invention are preferably used in the form of conductive layers or coatings in electrical or electronic components, light-emitting components, for antistatic coatings, in optoelectronics or in solar energy technology. These conductive layers are preferably produced by means of in-situ polymerization of the corresponding 3,4-alkylenedioxythiophenes according to the invention and one or more oxidants, in the presence or absence of additional counterions. The term "in-situ polymerization" is known to those skilled in the art.

In preferred embodiments, the conductive layers are subjected to a heat treatment to increase the conductivity.

The conductive layers can, for example, be produced by applying the 3,4-alkylenedioxythiophenes according to the invention, oxidants and, if desired, counterions, either together or in succession, if appropriate in the form of solutions, to the substrate to be coated and oxidatively polymerizing them by chemical means to give the novel polythiophenes and removing any solvent present either before, during or after the polymerization.

The application of the solutions to the substrate to be coated can be carried out by known methods, e.g. by steeping, casting, dribbling, spraying, spray coating, doctor blade coating, painting or printing.

The invention is further described by the following illustrative but non-limiting examples.

EXAMPLES

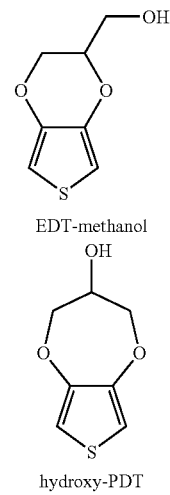

EDT-methanol hydroxy-PDT

The EDT-methanol/hydroxy-PDT mixture used below was prepared as described in U.S. Pat. No. 5,111,327. Cholesteryl chloroformate is commercially available; [(4'-cyano-1,1'-biphenyl-4-yl)oxy]acetic acid, [(4'-cyano-1,1'-biphenyl-4-yl)oxy]butyric acid and [(4'-cyano-1,1'-biphenyl-4-yl)oxy]valeric acid and [(4'-bromo-1,1'-biphenyl-4-yl)oxy]valeric acid were prepared as described in J. Am. Chem. Soc. 119 (1997), pp. 5825-5826.

Example 1

2.46 g of a mixture of 80% of EDT-methanol and 20% of hydroxy-PDT (corresponding to 11.5 mmol of EDT-methanol) are dissolved in dry methylene chloride and cooled in ice. 5.68 g (12.6 mmol) of cholesteryl chloroformate in dry methylene chloride are added to this cooled solution. 1.40 g (13.8 mmol) of triethylamine are then slowly added dropwise and the ice bath is removed. The reaction mixture is stirred at room temperature (23° C.) for 30 hours, and another 2.64 g (5.9 mmol) of cholesteryl chloroformate and 0.63 g (6.2 mmol) of triethylamine in methylene chloride are then added slowly. After a further reaction time of 72 hours, the solution is washed three times with 1 M (molar) HCl and three times with saturated NaHCO₃ solution. The organic phase is dried over MgSO₄ and the solvent is removed on a rotary evaporator at 20 mbar. The crude product is purified by chromatographing it twice on a column (eluant: 1. CHCl₃, 2. petroleum ether, eluted with CHCl₃). The product is recrystallized from acetone, giving 0.93 g of (I-a1) (in a mixture with 2% (I-b1); unless indicated otherwise, percentages are molar percentages) as a colourless powder.

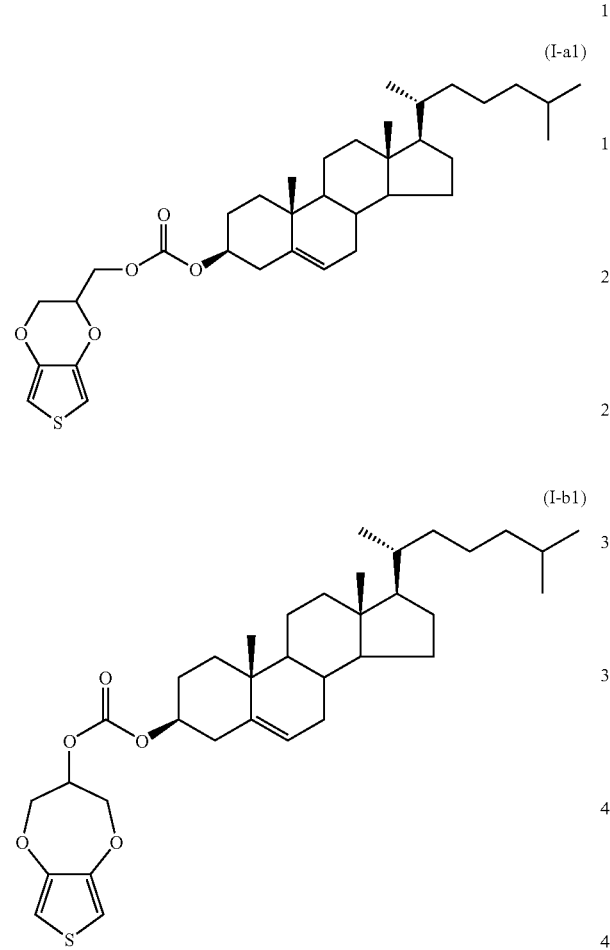

IR ν⁻¹ [cm⁻¹]=2939, 2902, 2867, 2848; 1740

¹H-NMR (200 MHz, CDCl₃): δ[ppm]=6.48 (s, 2% 2H, by-product I-b1); 6.35, 6.32 (2*d, each 98% 1H, $^4J_{CH—CH}$: 3.91 Hz); 5.38 (d, 1H); 4.62-4.15 (m, 5H); 4.26 (dd, 1H, $J_{CH—CH}$: 4.05 Hz); 2.38 (d, 2H); 2.17-0.73 (m, 38H); 0.99 (s, 3H); 0.89 (d, 3H); 0.84 (d, 6H); 0.66 (s, 3H)

¹³C-NMR (50.3 MHz, CDCl₃): δ [ppm]=154.16; 141.19; 140.93; 139.20; 123.14; 100.18, 99.98; 78.58; 71.26, 65.48; 65.18; 56.70; 56.16; 50.02; 42.34; 39.74; 39.53; 37.97; 36.85; 36.55; 36.21; 35.80; 31.92; 31.86; 28.23; 28.03; 27.66; 24.29; 23.85; 22.82; 22.59; 19.27, 18.74; 11.88

MS (FD, 5 kV): m/z=585.5, [M+H]⁺

Phase transitions (determined by means of a polarization microscope):
   m.p. 131.9° C., clearing point 137.5° C. (on 1st heating)

C 131.9 LC 137.5 I (C=crystalline, LC=liquid-crystalline, I=isotropic liquid; the numerical values between the phase designations indicate the transition temperature in ° C., e.g. C 131.9 LC=transition from the crystalline phase to the liquid-crystalline phase at 131.9° C.)

Example 2

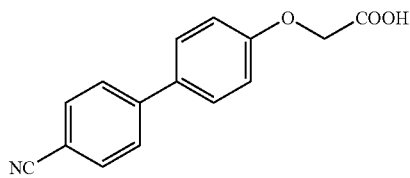

[(4'-cyano-1,1'-biphenyl-4-yl)oxy]acetic acid 1.73 g of a mixture of 80% of EDT-methanol and 20% of hydroxy-PDT (corresponding to 8.08 mmol of EDT-methanol), 1.64 g of N,N'-dicyclohexyl-carbodiimide and 0.13 g of 4-(dimethylamino)pyridine are dissolved in 100 ml of CH₂Cl₂ and cooled to about 0° C. in an ice bath. 2.00 g of [(4'-cyano-1,1'-biphenyl-4-yl)oxy]acetic acid are added thereto a little at a time over a period of 1 hour while stirring and cooling in ice. The reaction is then continued at 23° C. for 42.5 hours. The N,N'-dicyclohexylurea formed is subsequently filtered off. The filtrate is washed in succession with 2×200 ml of 1 M HCl, 2×200 ml of saturated NaHCO₃ solution and 2×200 ml of saturated NaCl solution. The organic phase is dried over MgSO₄ and, after the magnesium sulphate has been filtered off, freed of solvent on a rotary evaporator. This gives 3.71 g of crude product which is purified by column chromatography using n-hexane/ethyl acetate 3:2. 0.39 g of the pure ester of EDT-methanol (I-a2) is obtained as colourless crystals.

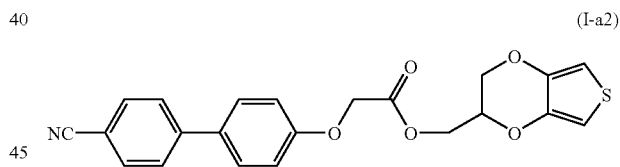

IR ν⁻¹ [cm⁻¹]=2992, 2979, 2942, 2909, 2226, 1751 and 1743, 1604, 1582 and 1495

¹H-NMR (500 MHz, DMSO-d₆): δ (ppm)=7.87 (d, 2H, $^3J_{CH—CH}$: 8.51 Hz,); 7.81 (d, 2H, $^3J_{CH—CH}$: 8.51 Hz); 7.68 (d, 2H, $^3J_{CH—CH}$: 8.83 Hz); 7.06 (d, 2H, $^3J_{CH—CH}$: 8.83 Hz); 6.61 (d, 1H, $^4J_{CH—CH}$: 3.78 Hz,); 6.58 (d, 1H, $^4J_{CH—CH}$: 3.78 Hz); 4.93 (s, 2H); 4.53-4.32 (m, 3H); 4.26 (dd, 1H, $J_{CH—CH}$: 11.67 Hz); 3.96 (dd, 1H, $J_{CH—CH}$: 11.67 Hz).

¹³C-NMR (125.75 MHz, DMSO-d₆): δ (ppm) 166.69; 156.38; 142.32; 139.28, 139.17, 130.99; 129.45; 126.53; 125.20; 117.19; 113.45; 107.52; 98.24, 98.20; 69.49; 63.03, 62.74; 60.70.

| MS (EI, 70 eV): m/e = | 407 | M⁺ | 100% |
|---|---|---|---|
| | 208 | C₁₄H₁₀NO⁺ | 24.3% |
| | 178 | C₁₃H₈N⁺ | 49.1% |
| | 155 | C₇H₇O₂S⁺ | 22.5% |

Melting range: 125.2-127.7° C. (observed under a polarization microscope).

Example 3

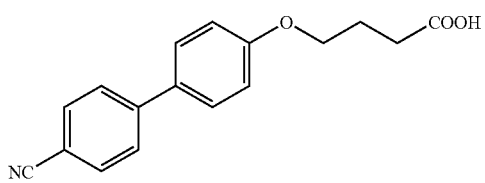

[(4'-cyano-1,1'-biphenyl-4-yl)oxy]butyric acid 1.06 g of a mixture of 80% of EDT-methanol and 20% of hydroxy-PDT (corresponding to 6.19 mmol; 4.95 mmol based on the main component EDT-methanol), 1.04 g (5.04 mmol) of N,N'-dicyclohexylcarbodiimide and 0.15 g (1.22 mmol) of 4-(dimethylamino)pyridine are dissolved in 50 ml of $CH_2Cl_2$ and cooled in an ice bath. 1.42 g (5.05 mmol) of [(4'-cyano-1,1'-biphenyl-4-yl)oxy]-butyric acid (see formula) are added in small doses while stirring to the ice-cooled solution. After 1 hour, the reaction is continued at room temperature. After a further 64 hours, the colourless precipitate (N,N'-dicyclohexylurea) formed is filtered off. The clear, colourless solution is washed in succession with 2×75 ml of 1 N HCl, 2×75 ml of saturated $NaHCO_3$ solution and 2×75 ml of NaCl solution. The clear organic phase is dried over $MgSO_4$, the desiccant is filtered off and the solvent is removed on a rotary evaporator. This gives 2.38 g of crude product.

Purification is carried out by column chromatography. Eluant: n-hexane/ethyl acetate 3:2.

Yield of (I-a3)/(I-b3): 1.25 g of colourless powder (56.8% of theory), 2 isomers: about 95% of (I-a3) and 5% of (I-b3).

(I-a3)

(I-b3)

Data for (I-a3)/(I-b3), molar ratio=95:5
IR $v^{-1}$ [cm$^{-1}$]=3117; 2969, 2947, 2923, 2905, 2884; 2222; 1734 1597, 1582, 1486; 827, 815

$^1$H-NMR (500 MHz, DMSO-d$_6$): δ [ppm]=7.86 (d, 2H); 7.81 (d, 2H); 7.68 (d, 2H, $^3J_{CH-CH}$: 8.83 Hz); 7.03 (d, 2H, $^3J_{CH-CH}$: 8.83 Hz); 6.79 (s, 5% 2H, (I-b3)); 6.58 (s, 95% 2H); 4.47-4.38 (m, 1H); 4.36-4.23 (m, 3H); 4.15 (d, 5% 4H, (I-b3)); 4.05 (t, 2H); 4.00 (dd, 1H); 2.55 (t, 2H); 2.02 (tt, 2H)

$^{13}$C-NMR (125.75 MHz, DMSO-d$_6$): δ [ppm]=172.46; 159.23; 144.36; 141.20; 141.11; 132.90; 130.58; 128.44; 126.97; 119.13; 115.23; 109.25; 100.08; 71.46; 66.72; 65.10; 62.24; 30.08; 24.22

| MS (EI, 70 eV): m/e = | 435 | M$^+$ | 39.8% |
|---|---|---|---|
| | 264 | $C_{17}H_{14}NO_2^+$ | 12.6% |
| | 241 | $C_{11}H_{13}O_4S^+$ | 44.5% |
| | 195 | $C_{13}H_8NO^+$ | 34.3% |
| | 155 | $C_7H_7O_2S^+$ | 100% |

Phase transitions (determined using a polarization microscope):

Melting range: 119.8-121.9° C. (on 1st heating), isotropic at 118.8° C. on 2nd heating C 116.9 LC 117.0 I (on 3rd heating)

Example 4

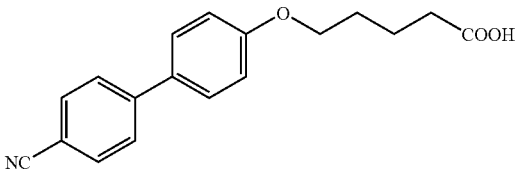

[(4'-cyano-1,1'-biphenyl-4-yl)oxy]valeric acid 2.20 g of a mixture of 80% of EDT-methanol and 20% of hydroxy-PDT (corresponding to 12.9 mmol; 10.3 mmol based on the main component EDT-methanol), 2.10 g (10.2 mmol) of N,N'-dicyclohexylcarbodiimide and 1 spatula tip of 4-(dimethylamino)pyridine are dissolved in 80 ml of $CH_2Cl_2$ and cooled in an ice bath. 3.00 g (10.2 mmol) of [(4'-cyano-1,1'-biphenyl-4-yl)oxy]valeric acid (see formula) are added a spatula at a time to the cold (0° C.) solution while stirring. Remaining [(4'-cyano-1,1'-biphenyl-4-yl)oxy]valeric acid is dissolved in 20 ml of $CH_2Cl_2$ and added to the reaction. After 1 hour, the reaction is continued at room temperature. After a further 48 hours, the colourless precipitate formed (N,N'-dicyclohexylurea) is filtered off. The clear, colourless solution is washed in succession with 3×75 ml of 1 N HCl, 3×75 ml of saturated $NaHCO_3$ solution and 3×75 ml of saturated NaCl solution. The organic phase is dried over $MgSO_4$, the desiccant is filtered off and the solvent is removed on a rotary evaporator. This gives 4.70 g of crude product.

Purification is carried out by column chromatography. Eluant: n-hexane/ethyl acetate 3:2.

Yield of pure product (2 isomers: about 97% of (I-a4) and 3% of (I-b4)):

1.40 g of colourless powder (30.7% of theory)

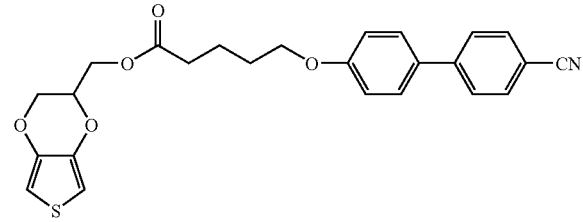
(I-a4)

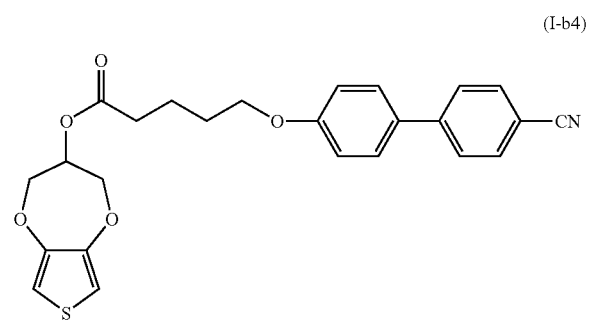
(I-b4)

Data for (I-a4)/(I-b4), molar ratio=97:3

IR $\nu^{-1}$ [cm$^{-1}$]=3122, 3109; 2962, 2938, 2918, 2879, 2864; 2220; 1733; 1600, 1579, 1481; 826.

$^1$H-NMR (500 MHz, DMSO-d$_6$): δ [ppm]=7.85 (d, 2H, $^3J_{CH-CH}$: 8.52 Hz); 7.81 (d, 2H, $^3J_{CH-CH}$: 8.52 Hz); 7.67 (d, 2H, $^3J_{CH-CH}$: 8.83 Hz); 7.03 (d, 2H, $^3J_{CH-CH}$: 8.83 Hz); 6.79 (s, 3% 2H, (I-b4)); 6.59 (s, 97% 2H); 4.44-4.36 (m, 1H); 4.33-4.20; 4.09-3.94 (2*m, 2*3H); 4.14 (d, 3% 4H, (I-b4)); 2.43 (t, 2H); 1.83-1.62 (m, 4H)

$^{13}$C-NMR (125.75 MHz, DMSO-d$_6$): δ [ppm]=172.92; 159.62; 144.62; 141.46; 133.12; 130.67; 128.65; 127.17; 119.37; 115.44; 109.45; 100.30; 71.70; 67.56; 65.33; 62.32; 33.24; 28.25; 21.44

Phase transitions (determined using a polarization microscope):

C 103.0 LC 105.8 I (on 1st heating, start at 95° C., heating rate <1° C./min)

| MS (EI, 70 eV): m/e = | 449 | M$^+$ | 25.1% |
|---|---|---|---|
| | 255 | C$_{12}$H$_{15}$O$_4$S$^+$ | 68.9% |
| | 195 | C$_{13}$H$_9$NO$^+$ | 31.2% |
| | 155 | C$_7$H$_7$O$_2$S$^+$ | 100% |

Example 5

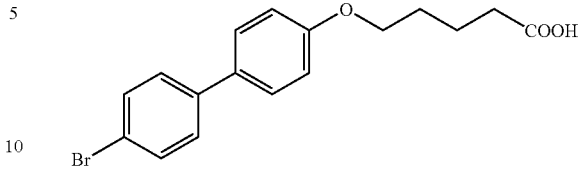

[(4'-bromo-1,1'-biphenyl-4-yl)oxy]valeric acid 3.26 g of a mixture of 80% of EDT-methanol and 20% of hydroxy-PDT (corresponding to 18.9 mmol; 15.1 mmol based on the main component EDT-methanol), 3.14 g (15.2 mmol) of N,N'-dicyclohexylcarbodiimide and 0.3 g (2.45 mmol) of 4-(dimethylamino)pyridine are dissolved in 100 ml of CH$_2$Cl$_2$ and cooled in an ice bath. 5.25 g (15.0 mmol) of [(4'-bromo-1,1'-biphenyl-4-yl)oxy]-valeric acid are added a spatula at a time to the ice-cooled solution while stirring. After 1 hour, the reaction is continued at room temperature. After a further 65 hours, the colourless precipitate formed (N,N'-dicyclohexylurea) is filtered off. The clear, colourless solution is washed in succession with 3×250 ml of 1 N HCl, 3×150 ml of saturated NaHCO$_3$ solution and 1×150 ml and 2×100 ml of saturated NaCl solution. The organic phase is dried over MgSO$_4$, the desiccant is filtered off and the solvent is removed on a rotary evaporator. This gives 7.98 g of crude product.

Purification is carried out by column chromatography. Eluant: n-hexane/ethyl acetate 4:1.

Yield of (I-a5) (contains about 5% of isomer (I-b5)):

3.06 g of colourless powder (6.08 mmol=40.5% of theory)

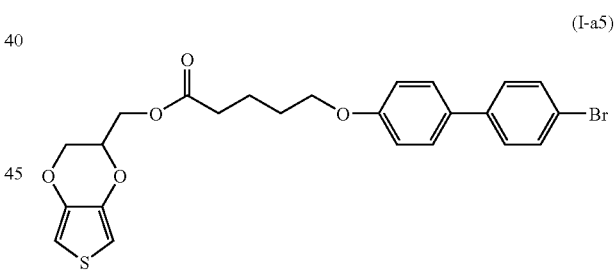
(I-a5)

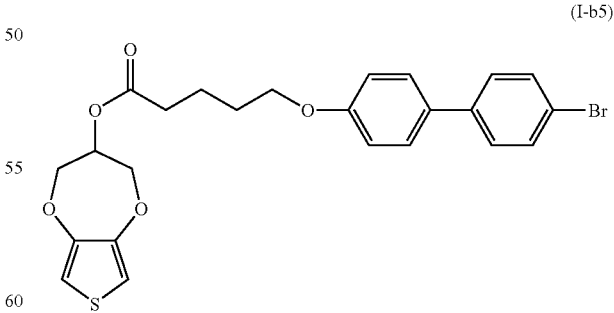
(I-b5)

Data for (I-a5):

IR $\nu^{-1}$ [cm$^{-1}$] 3108; 2956, 2933, 2905, 2868, 1740; 1606, 1579, 1488; 815

$^1$H-NMR (500 MHz, DMSO-d$_6$): δ [ppm]=7.65-7.50 (m, 6H); 6.99 (d, 2H); 6.79 (s, 5% 2H), 6.59 (s, 95% 2H); 4.44-

4.36 (m, 1H); 4.33-4.19; 4.17-4.12 (m, 5% 4H); 4.07-3.94 (2*m, 2*3H); 2.43 (t, 2H); 1.81-1.63 (m, 4H)

$^{13}$C-NMR (125.75 MHz, DMSO-d$_6$): δ [ppm]=172.92; 158.88; 141.46; 141.35; 139.37; 132.04; 131.43; 128.57; 128.05; 120.34; 115.32; 100.30; 71.70; 67.49; 65.33; 62.32; 33.25; 28.29; 21.46

Phase Transitions:

Liquid-crystalline phases were observed under a polarization microscope.

DSC:

1st heating: onset: 98.50° C., maximum: 100.68° C., endset: 103.63° C., heating rate: 5° C./min, hold for 5 minutes at 130° C.

1st cooling:

1st peak: onset: 82.41° C., minimum: 82.39° C., endset: 81.58° C.,

2nd peak: onset: 81.01° C., minimum: 81.00° C., endset: 80.75° C., heating rate: −1° C./min 2nd heating:

1st peak: onset: 82.43° C., maximum: 84.00° C., endset: 85.35° C.,

2nd peak: onset: 92.75° C., minimum: 94.57° C., endset: 96.00° C., heating rate: 2° C./min

| MS (EI, 70 eV): m/e = | 502 | M$^+$ | 37.4% |
|---|---|---|---|
| | 255 | C$_{12}$H$_{15}$O$_4$S$^+$ | 86.0% |
| | 248 | C$_{12}$H$_{10}$BrO$^+$ | 22.1% |
| | 155 | C$_7$H$_7$O$_2$S$^+$ | 100.0% |

Example 6

Uncharged Polythiophene Prepared from (I-a5) and (I-b5)

0.3 g (0.6 mmol) of the thiophene mixture prepared as described in Example 5 (I-a5/I-b5, molar ratio=95:5) is dissolved in 12 ml of chloroform. 0.15 g (1.5 mmol) of finely powdered calcium carbonate is slurried in this solution. 0.24 g (1.48 mmol) of iron(III) chloride (anhydrous) is added in two equal portions to this mixture 1 hour apart while stirring at 23° C. The mixture is stirred for another 4 hours at 23° C. 12 ml of methylene chloride are then added. After addition of 6 ml of aqueous ammonia (26%), the mixture is refluxed for 2 hours. The solid is subsequently filtered off. The solid is washed with chloroform and the combined organic phases are once again refluxed with 6 ml of aqueous 26% ammonia for 1 hour while stirring vigorously. The organic phase is washed with 0.05 mol EDTA solution (Na ethylenediaminetetraacetate) and subsequently washed with water, dried over sodium sulphate and evaporated. The solid residue is boiled in methanol for 30 minutes and filtered off hot. This gives 0.13 g (43.3% of theory) of polythiophene comprising recurring units (IV-a5) and (IV-b5).

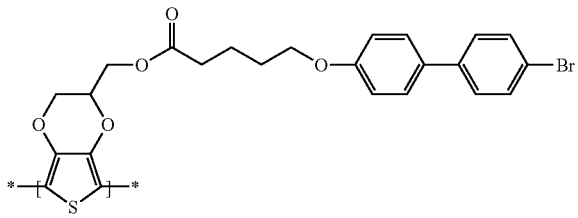

(IV-a5)

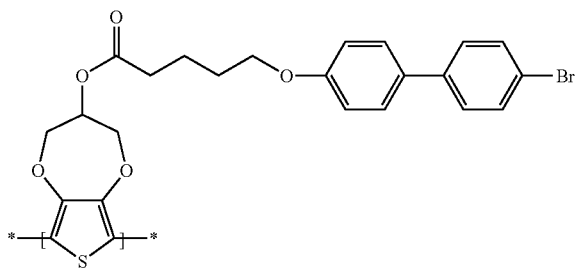

(IV-b5)

Characterization by MALDI-TOF-MS (FIG. 1).

Example 7

Uncharged Polythiophene Prepared from (I-a5) and (I-b5)

0.6 g (1.19 mmol) of the thiophene prepared as described in Example 5 (I-a5/I-b5, molar ratio=95:5) is dissolved in 24 ml of chloroform. 0.475 g (4.75 mmol) of finely powdered calcium carbonate is slurried in this solution. 0.77 g (4.75 mmol) of iron(III) chloride (anhydrous) is added in three equal portions to this mixture at intervals of 1 hour while stirring at 23° C. The mixture is stirred for another 4 hours at 23° C. 24 ml of methylene chloride are then added. After addition of 12 ml of aqueous ammonia (26%), the mixture is refluxed for 2 hours. The solid is subsequently filtered off. The solid is washed with chloroform and the combined organic phases are once again refluxed with 12 ml of aqueous 26% ammonia for 1 hour while stirring vigorously. The organic phase is washed with 0.05 mol EDTA solution (Na ethylenediaminetetraacetate) and subsequently washed with water, dried over sodium sulphate and evaporated. The solid residue is boiled in methanol for 30 minutes and filtered off hot. This gives 0.2 g (33.3% of theory) of polythiophene comprising recurring units (IV-a5) and (IV-b5).

Characterization by Gel Permeation Chromatography (in THF, Polystyrene Standard, RI Detection): M$_n$=2300; M$_w$=9900

Example 8

Cationic, Highly Conductive Polythiophene from (I-a5) and (I-b5) as Coating by In-Situ Polymerization 0.22 g of the thiophene prepared as described in Example 5 (I-a5/I-b5, molar ratio=95:5) is dissolved in 6.625 g of boiling n-butanol. 1.562 g of a 40% solution of iron(III) tosylate in n-butanol (Baytron® CB 40; manufacturer: H. C. Starck GmbH) are added quickly to the hot solution and the mixture is applied by doctor blade coating to a glass plate which has been preheated to about 100° C. (wet film thickness 24 μm). After drying at 100° C. for 10 minutes and cooling to room temperature (23° C.), the coating is washed with deionized water and dried by means of a hot air dryer. The surface resistance (two-point method) is measured as 461 Ω/square. The plate was annealed again at 150° C. for 30 minutes, and the surface resistance after cooling to 23° C. was measured as 211 Ω/square.

Example 9

Cationic Polythiophene (Tetrachloroferrate) from (I-a5) and (I-b5) as Powder 1.0 g (1.99 mmol) of the thiophene prepared as described in Example 5 (I-a5/I-b5, molar ratio=95:5) is dissolved in 7.7 ml of acetonitrile under $N_2$ and the solution is heated to reflux. 1.875 g (11.56 mmol) of iron(III) chloride (anhydrous) in 19 ml of acetonitrile are added dropwise to this solution over a period of 30 minutes under reflux. The solution is refluxed for a further 16 hours. The insoluble precipitate of cationic polythiophene is subsequently filtered off with suction and washed a number of time with acetonitrile. Yield: 0.89 g of cationic polythiophene having tetachloroferrate as counterion.

Example 10 a) Reaction of an EDT-Methanol/Hydroxy-PDT Mixture with 1,6-dibromohexane (Reactant Containing the Group B)

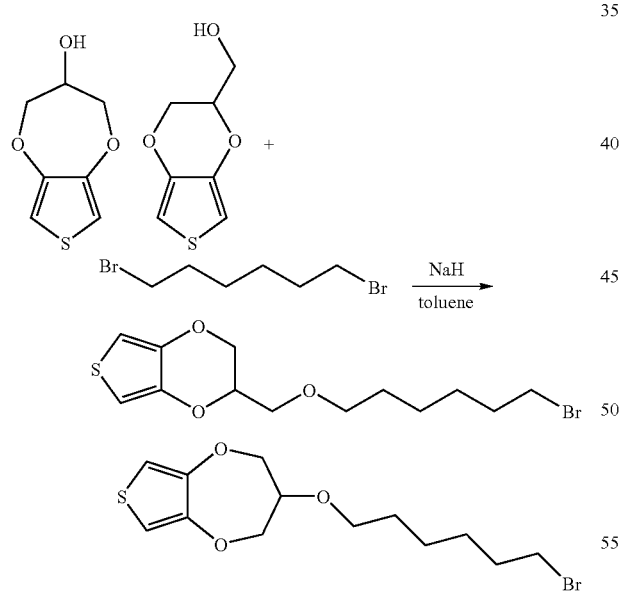

The reaction is carried out under a protective Ar atmosphere. 3.03 g of sodium hydride (60% in mineral oil, 75.8 mmol) are washed twice with dry toluene and then suspended in 100 ml of toluene. The suspension is heated to 80° C. and 10 g of EDT-methanol/hydroxy-PDT (80:20, 58.1 mmol (based on the mixture)) dissolved in 80 ml of toluene are slowly added dropwise over a period of 40 minutes. The colourless suspension becomes yellowish brown. After a further hour, 70.9 g (290.5 mmol) of 1,6-dibromohexane are added. The solution is stirred at 80° C. for 100 minutes, and the heating is then switched off and the solution is stirred at room temperature (23° C.) for a further 20 hours. 15 ml of acetone are added and after half an hour, 8 ml of water are added. This results in dissolution of the colourless precipitate and two phases are formed. The reaction mixture is washed twice with 90 ml each time of 1 molar (M) HCl. The toluene phase is extracted with 180 ml of 1 M HCl. The collected HCl phases are extracted three times with 90 ml of chloroform. The collected chloroform phases are discarded and the HCl phase is extracted three times with 50 ml of toluene. The HCl phase is then discarded. The collected toluene phases are washed three times with 120 ml each time of saturated aqueous NaCl solution. The toluene phase is dried over $MgSO_4$, the desiccant is filtered off and the solvent is removed on a rotary evaporator. The brown liquid obtained in this way is purified by column chromatography (ethyl acetate:hexane, initially 1:19, and later 1:4).

Yield: 12.95 g (38.6 mmol (based on the mixture)=66.5% of theory) of yellowish crystals. Content of PDT derivative: 16%.

b) Reaction of the Product Mixture from a) with 4-(4-bromophenyl)phenol (Reactant Containing the Group M)

1.13 g (4.54 mmol) of 4-(4-bromophenyl)phenol, 1.69 g (5.04 mmol) of the product mixture from a) (16% of PDT derivative, 84% of EDT derivative) and 1.81 g (5.56 mmol) of $Cs_2CO_3$ are suspended in 30 ml of DMF and stirred at room temperature for 70 hours. 90 ml of pH 7 buffer (Aldrich) are added to the suspension and the solution is extracted twice with 100 ml each time of diethyl ether. The collected ether phases are dried over $MgSO_4$, the desiccant is filtered off and the solvent is removed on a rotary evaporator. The crude product is recrystallized from methanol/methylene chloride. The colourless crystals obtained are filtered off, washed with methanol and dried over $P_2O_5$ under reduced pressure.

Yield: 1st fraction: 1.57 g (3.12 mmol 68.7% of theory) of colourless crystals of (I-a6) in admixture with 14% of (I-b6). 2nd fraction: 0.33 g (0.66 mmol=14.4% of theory) of colourless, platelet-like crystals of (I-a6) in admixture with 15 mol % of (I-b6).

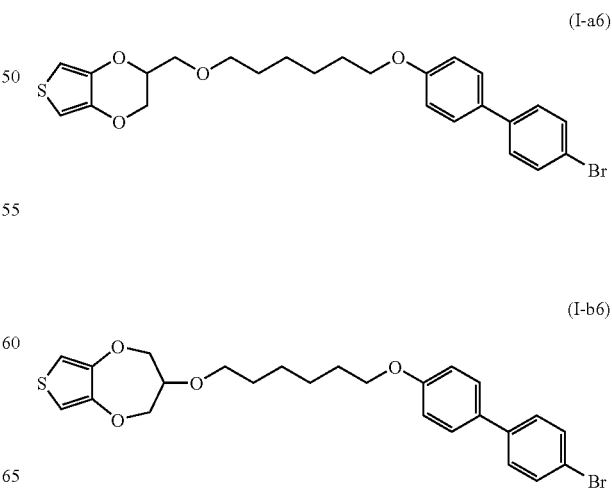

IR ν⁻¹ [cm⁻¹]=2934, 2868, 2859, 1604, 1580, 1491, 806.

¹H-NMR (500 MHz, CDCl₃): δ [ppm] 7.52 (d, 2H, ³J$_{CH-CH}$: 8.51 Hz); 7.47 (d, 2H, ³J$_{CH-CH}$: 8.83 Hz); 7.41 (d, 2H, ³J$_{CH-CH}$: 8.51 Hz); 6.95 (d, 2H, ³J$_{CH-CH}$: 8.83 Hz); 6.46 (s, 14% 2H); 6.33, 6.32 (2*d, each 86% 1H); 4.34-4.27 (m, 86% 1H); 4.27-4.20 (m, 86% 1H); 4.10 (dd, 14% 4H); 4.05 (dd, 86% 1H); 3.99 (t, 2H); 3.87-3.80 (m, 14% 1H); 3.69 (dd, 86% 1H, J$_{CH-CH}$: 10.40 Hz); 3.60 (dd, 86% 1H, J$_{CH-CH}$: 10.40 Hz); 3.56 (t, 14% 1H); 3.51 (t, 86% 2H); 1.81 (m, 2H); 1.63 (m, 2H); 1.54-1.39 (2*m, each 2H)

¹³C-NMR (125.75 MHz, DMSO-d⁶): δ [ppm]=158.97; 149.42; 141.73, 141.67; 139.37; 132.03; 131.34; 128.54, 128.04; 120.32; 115.30; 105.92; 100.04, 99.97; 77.34, 71.61, 68.91; 72.82, 71.16, 68.87, 67.82, 65.85; 29.71; 29.35, 28.98; 25.69.

Phase Transitions (Determined Using a Polarization Microscope):
C 86.2 LC 87.7 I (on 1st heating)
C 86.2 LC 88.1 I (on 2nd heating)

| MS (El, 70 eV): m/e = | 502 | M⁺ | 96.6% |
|---|---|---|---|
| | 248 | C₁₂H₉BrO⁺ | 63.5% |
| | 172 | C₇H₈O₃S⁺ | 19.8% |
| | 83 | C₄H₃S⁺ | 64.6% |

Example 11 a) Preparation of a Reactant Containing the Group M

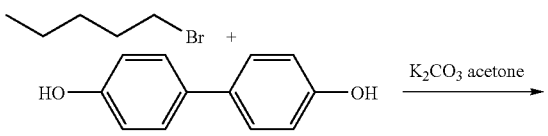

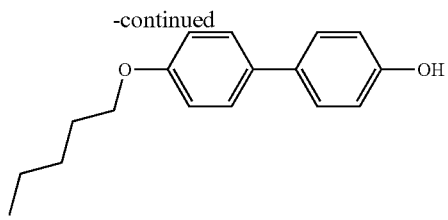

3.22 g (17.3 mmol) of 4,4'-dihydroxybiphenyl, 2.62 g (17.3 mmol) of 1-bromo-pentane and 2.53 g (18.3 mmol) of K₂CO₃ are suspended in 150 ml of acetone and refluxed for 26 hours, after which the mixture is stirred at room temperature for a further 24 hours. The precipitate is filtered off, discarded and the acetone is removed completely from the filtrate on a rotary evaporator. The yellowish precipitate formed is purified by column chromatography (4 parts hexane: 1 part ethyl acetate).

Yield: 2.07 g (8.08 mmol=46.7% of theory) of cream-coloured crystals.

b) Reaction of the Product Mixture from Example 10a) with the Reactant from Example 11a)

0.50 g (1.95 mmol) of the reactant from Example 11a), 0.75 g (2.24 mmol) of the product mixture from Example 10a) (16% of PDT derivative, 84% of EDT derivative) and 0.76 g (2.33 mmol) of Cs₂CO₃ are suspended in 15 ml of DMF and stirred at room temperature for 5 days. 50 ml of saturated aqueous NaHCO₃ solution are added to the suspension and the mixture is extracted twice with 50 ml each time of chloroform. The collected chloroform phases are washed again with 50 ml of saturated aqueous NaHCO₃ solution; the chloroform phase is then washed twice with 50 ml each time of saturated aqueous NaCl solution. The chloroform phase is dried over MgSO₄, the desiccant is filtered off and the solvent is removed on a rotary evaporator. The crude product is recrystallized from methanol/methylene chloride. The beige crystals obtained are filtered off, washed with methanol and dried over P₂O₅ under reduced pressure.

Yield: 0.87 g (1.7 mmol=87.4% of theory (based on the mixture)) of (I-a7) in admixture with 15.5% of (I-b7)

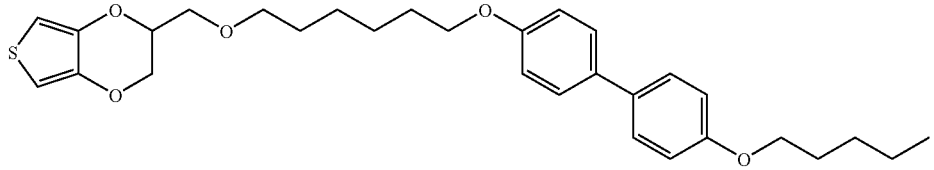
(I-a7)

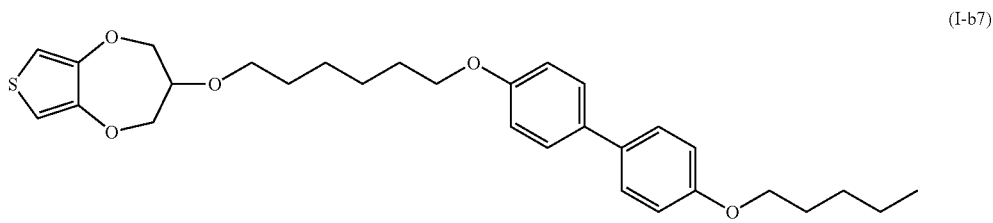
(I-b7)

IR ν⁻¹ [cm⁻¹]=3040, 3067, 2957, 2936, 2861, 1606, 1568, 1491, 807.

¹H-NMR (500 MHz, CDCl₃): δ [ppm]=7.51-7.41 (m, 4H); 6.99-6.89 (m, 4H); 6.46 (s, 15.5% 2H); 6.33, 6.32 (2*d, 84.5% 2H); 4.33-4.27 (m, 84.5% 1H); 4.26-4.20 (m, 84.5% 1H); 4.09 (dd, 15.5% 4H); 4.05 (dd, 84.5% 1H); 3.98 (t, 4H, 13-H); 3.86-3.80 (m, 15.5% 1H); 3.68 (dd, 84.5% 2H, $J_{CH-CH}$: 10.40 Hz); 3.59 (dd, 84.5% 2H, $J_{CH-CH}$: 10.40 Hz); 3.55 (t, 15.5% 1H); 3.51 (t, 84.5% 2H); 1.86-1.74 (m, 4H); 1.63 (m, 2H); 1.55-1.33 (m, 8H); 0.94 (t, 3H).

¹³C-NMR (125.75 MHz, CDCl₃: δ [ppm]=157.20, 157.12; 148.11; 140.57, 140.53; 132.35 132.25; 126.62; 113.69; 104.25; 98.65, 98.53; 76.83, 70.64; 71.62, 70.87, 68.10, 67.03, 66.85, 65.19; 28.80; 28.45, 28.22, 27.98, 27.20; 24.87, 24.81; 21.46; 13.03.

Phase Transitions (Determined Using a Polarization Microscope):
C 101.1 LC 103.1 I (on 1st heating, start 92° C., <1° C./min)

| MS (EI, 70 eV): m/e = | 510 | M⁺ | 100.0% |
|---|---|---|---|
| | 256 | $C_{17}H_{20}O_2^+$ | 10.8% |
| | 186 | $C_{12}H_{10}O_2^+$ | 51.9% |
| | 83 | $C_4H_3S^+$ | 15.3% |

Example 12 a) Reaction of an EDT-Methanol/Hydroxy-PDT Mixture with 1,5-dibromopentane (Reactant Containing the Group B)

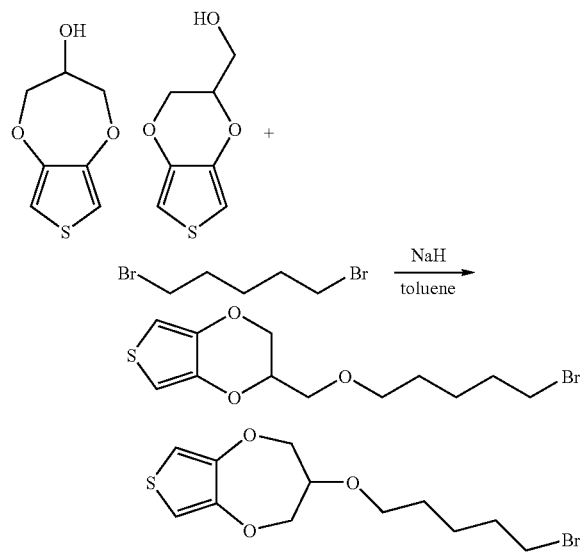

The reaction is carried out under nitrogen. 8 g of sodium hydride (60% in mineral oil, 0.2 mol) are washed twice with dry toluene and then suspended in 200 ml of toluene. The suspension is heated to 80° C. and 20 g of EDT-methanol/hydroxy-PDT (80:20, 116.2 mmol, based on the mixture) dissolved in 160 ml of toluene are added dropwise over a period of 1.5 hours. The colourless suspension becomes brown. After a further hour, 134 g (581 mmol) of 1,5-dibromopentane are added. The solution is stirred at 80° C. for 2 hours, and the heating is then switched off and the solution is stirred at room temperature for a further 12 hours. 16 ml of water are carefully added to stop the reaction. The reaction mixture is washed twice with 180 ml each time of 1 N HCl. The toluene phase is washed again with 360 ml of 1 N HCl. The collected HCl phases are extracted three times with 180 ml of chloroform. The collected chloroform phases are discarded and the HCl phase is extracted three times with 100 ml of toluene. The HCl phase is then discarded. The collected toluene phases are washed three times with 240 ml each time of saturated aqueous NaCl solution. The toluene phase is dried over MgSO₄, the desiccant is filtered off and the solvent is removed on a rotary evaporator. The excess 1,5-dibromopentane is distilled off at 60° C. under a high vacuum. The crude product is purified by column chromatography (ethyl acetate:hexane 1:4).

Yield: 19.49 g (60.7 mmol=52.1% of theory) of greenish oil, content of PDT derivative: 7% b) Reaction of the Product Mixture from a) with 4-(4-bromophenyl)phenol (Reactant Containing the Group M)

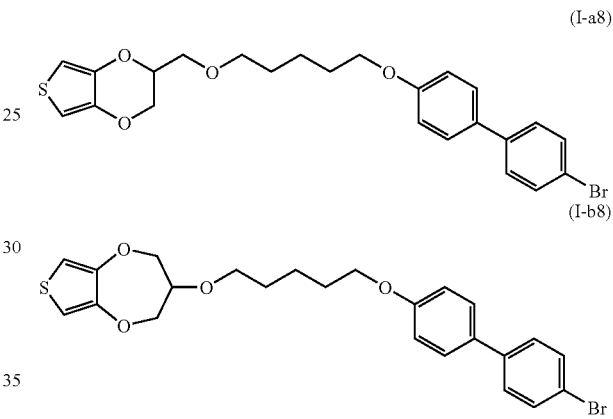

1.43 g (5.74 mmol) of 4-(4-bromophenyl)phenol, 1.93 g (6.01 mmol) of the product mixture from a) (7% of PDT derivative, 93% of EDT derivative) and 2.56 g (7.86 mmol) of Cs₂CO₃ are suspended in 50 ml of DMF and stirred at room temperature for 4 days. The work-up is carried out in a manner analogous to Example 10b).

The crude product is recrystallized from methanol/methylene chloride. The colourless precipitate is filtered off, washed with methanol and dried under reduced pressure.

Yield: 1st fraction: 1.87 g (3.82 mmol=66.6% of theory) of (I-a8) in admixture with 5% of (I-b8) 2nd fraction: 0.57 g (1.17 mmol=20.3% of theory) of (I-a8) in admixture with 9% (I-b8) 3rd fraction 0.17 g (0.35 mmol=6.1% of theory) of (I-a8) in admixture with 31% (I-b8).

IR ν⁻¹ [cm⁻¹]=2942, 2912, 2870 1604, 1579, 1482 816.

¹H-NMR (500 MHz, CDCl₃): δ [ppm]=7.52, 7.40 (2*d, each 2H); 7.46 (d, 2H); 6.95 (d, 2-H); 6.46 (s, 5% 2H); 6.33, 6.32 (2*d, each 95% 1H); 4.36-4.27 (m, 95% 1H); 4.24 (dd, 95% 1H, $J_{CH-CH}$: 11.67 Hz, superimposed dd); 4.10 (dd, 5% 2H); 4.06 (dd, 95% 1H, $J_{CH-CH}$: 11.67 Hz); 3.99 (t, 2H); 3.88-3.80 (m, 5% 1H); 3.69 (dd, 95% 1H, $J_{CH-CH}$: 10.40 Hz); 3.60 (dd, 95% 1H, $J_{CH-CH}$: 10.40 Hz); 3.53 (t, 95% 2H); 1.83, 1.67 (2*m, each 2H); 1.62-1.47 (m, 2H)

¹³C-NMR (125.75 MHz, CDCl₃): δ [ppm]=159.28; 141.98, 141.94; 140.16; 132.73; 132.17; 128.67, 128.35; 121.13; 115.27; 100.10; 99.98; 73.04, 72.20; 69.58, 68.25, 66.61; 29.69, 29.44; 23.08

Phase Transitions (Determined Using a Polarization Microscope):
C 109.1° C. LC about 120° C. I (1st heating)
C 107.7° C. LC about 126° C. I (2nd heating)

Elemental Analysis:

| Calculated: | 58.90% C | 5.15% H |
|---|---|---|
| Found: | 59.11% C | 5.11% H |

| MS (EI, 70 eV): m/e = | 488 | $M^+$ | 38.9% |
|---|---|---|---|
| | 241 | $C_{12}H_{17}O_3S^+$ | 54.7% |
| | 155 | $C_7H_7O_2S^+$ | 38.6% |

Example 13

Cationic, Highly Conductive Polythiophene from (I-a8) and (I-b8) as Coating by In-Situ Polymerization 0.21 g of the thiophene prepared as described in Example 12 (I-a8)/(I-b8) (molar ratio=95:5) is dissolved in 6.625 g of hot n-butanol. 1.562 g of a 40% strength solution of iron(III) tosylate in n-butanol (Baytron® CB 40; manufacturer: H. C. Starck GmbH) are added quickly to the hot solution and the mixture is applied by doctor blade coating to a glass plate which had been preheated to about 80° C. (wet film thickness: 24 μm). After drying at 80° C. for 10 minutes and cooling to room temperature (23° C.), the coating is washed with deionized water and dried by means of a hot air dryer. The surface resistance (two-point method) is measured as 601 Ω/square. The plate is annealed at 150° C. for 30 minutes, and the surface resistance after cooling to 23° C. is measured as 190 Ω/square.

Example 14 a) Reaction of an EDT-Methanol/Hydroxy-PDT Mixture with 1,6-dibromohexane (Reactant Containing the Group B)

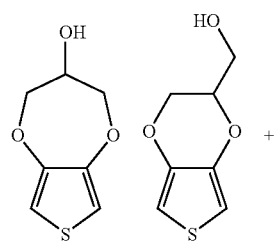

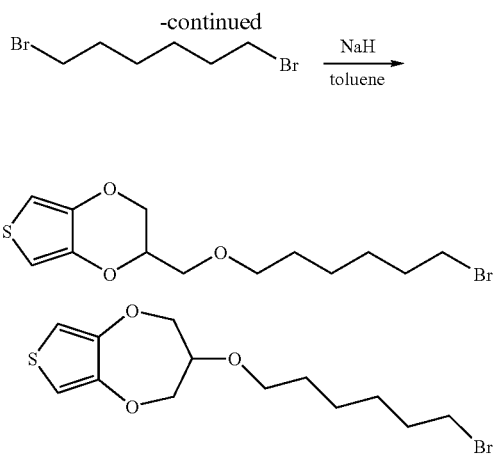

The reaction is carried out in a manner corresponding to Example 10a).

b) Reaction of the Product Mixture from a) with 4-(4-propylphenyl)benzoic acid (Reactant Containing the Group M)

1.00 g (4.16 mmol) of 4-(4-propylphenyl)benzoic acid, 1.57 g (4.68 mmol) of the product mixture from a) (16% of PDT derivative, 84% of EDT derivative) and 1.67 g (5.13 mmol) of $Cs_2CO_3$ are suspended in 46 ml of DMF and stirred at room temperature for 5 days. 50 ml of saturated aqueous $NaHCO_3$ solution are added to the suspension, and the solution is extracted twice with 50 ml each time of chloroform. To improve the phase separation, 50 ml of water are added. The collected organic phases are washed again with 75 ml of aqueous $NaHCO_3$ solution and then washed twice with 50 ml each time of saturated aqueous NaCl solution. The chloroform phase is dried over $MgSO_4$, the desiccant is filtered off and the solvent is removed on a rotary evaporator and in an oil pump vacuum.

The beige crude product is purified by column chromatography (eluant: hexane/ethyl acetate 4:1). This gives a clear liquid which crystallizes in the freezer to give a colourless precipitate.

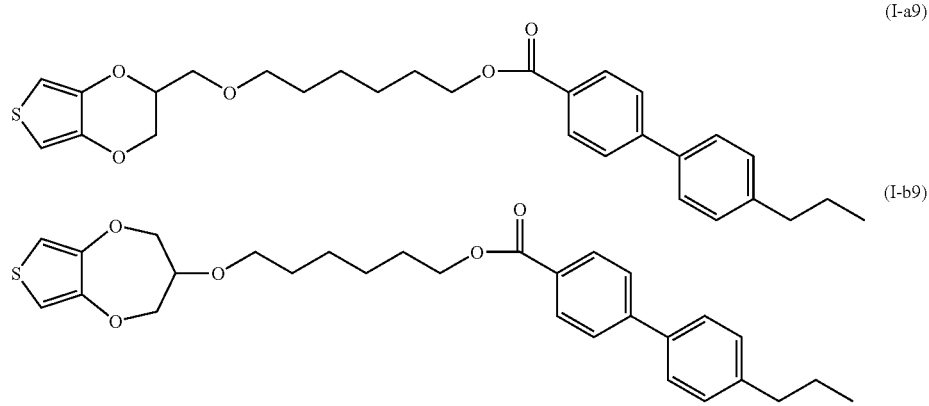

Yield: 2.00 g (4.04 mmol=97% of theory) of (I-a9) in admixture with 15% of (I-b9)

IR ν$^{-1}$ [cm$^{-1}$]=2931, 2866; 1711; 1607, 1580, 1485; 835

$^1$H-NMR (500 MHz, CDCl$_3$): δ [ppm]=8.09 (d, 2H); 7.65 (d, 2H); 7.54, 7.28 (2*d, each 2H); 6.46 (s, 15% 2H); 6.33, 6.31 (2*d, each 85% 1H, $^4$J$_{CH-CH}$: 3.47 Hz); 4.34 (t, 2H); 4.32-4.26 (m, partly superimposed 85% 1H); 4.23 (dd, 85% 1H superimposed dd); 4.09 (dd, superimposed; 15% 2H); 4.05 (dd, 85% 1H); 3.87-3.80 (m, 15% 1H); 3.68 (dd, 85% 1H, J$_{CH-CH}$: 10.40 Hz); 3.59 (dd, 85% 1H, J$_{CH-CH}$: 10.40 Hz); 3.55 (t, 85% 1H); 3.51 (t, 85% 2H); 2.64 (t, 2H); 1.85-1.74 (m, 2H); 1.74*1.56 (m, 4H); 1.54-1.37 (m, 4H); 0.97 (t, 3H)

$^{13}$C-NMR (125.75 MHz, CDCl$_3$): δ [ppm]=166.60; 145.53, 142.60, 137.34; 141.57, 141.54; 130.02, 129.06, 127.08, 126.79; 128.87; 99.67, 99.55; 77.88; 72.53, 71.87; 71.65, 69.82; 69.14, 66.21, 64.91; 37.70; 29.80; 29.44, 28.72; 25.90, 25.76; 24.52; 13.86

Phase Transitions (Determined Using a Polarization Microscope):

C 49.1° C. LC 56.4° C. I (1st heating, <1° C./min)

C 53.1° C. LC 58.1° C. I (2nd heating, <1° C./min)

Phase Transitions (Determined by DSC):

1st heating: onset: 50.58° C., maximum: 53.19° C., endset: 57.38° C.,

2nd heating: onset: 46.88° C., maximum: 49.35° C., endset: 52.77° C.,

3rd heating: onset: 45.25° C., maximum: 49.44° C., endset: 52.82° C., heating rate always 1° C./min Elemental Analysis:

| calculated: | 70.42% C | | 6.93% H | |
|---|---|---|---|---|
| found: | 70.49% C | | 6.91% H | |
| MS (EI, 70 eV): m/e = | 494 | M$^+$ | | 7.6% |
| | 255 | C$_{13}$H$_{10}$O$_3$S$^+$ | | 11.2% |
| | 223 | C$_{16}$H$_{15}$O$^+$ | | 24.3% |
| | 83 | C$_4$H$_3$S$^+$ | | 32.4% |

Example 15

Cationic, Highly Conductive Polythiophene from (I-a9) and (I-b9) as coating by in-situ polymerization 0.215 g of the thiophene prepared as described in Example 14 (I-a9)/(I-b9) (molar ratio=85:15) is dissolved in 6.625 g of warm n-butanol. 1.562 g of a 40% solution of iron(III) tosylate in n-butanol (Baytron® CB 40; manufacturer: H. C. Starck GmbH) are added quickly to the solution and the mixture is applied by doctor blade coating to a glass plate which has been preheated to about 80° C. (wet film thickness: 24 μm). After drying at 80° C. for 10 minutes and cooling to room temperature (23° C.), the coating is washed with deionized water and dried by means of a hot air dryer. The surface resistance (two-point method is measured as 473 Ω/square.

The plate is annealed at 150° C. for 30 minutes, and the surface, resistance after cooling to 23° C. is measured as 110 Ω/square.

Example 16 a) Reaction of an EDT-Methanol/Hydroxy-PDT Mixture with 1,4-dibromobutane (Reactant Containing the Group B)

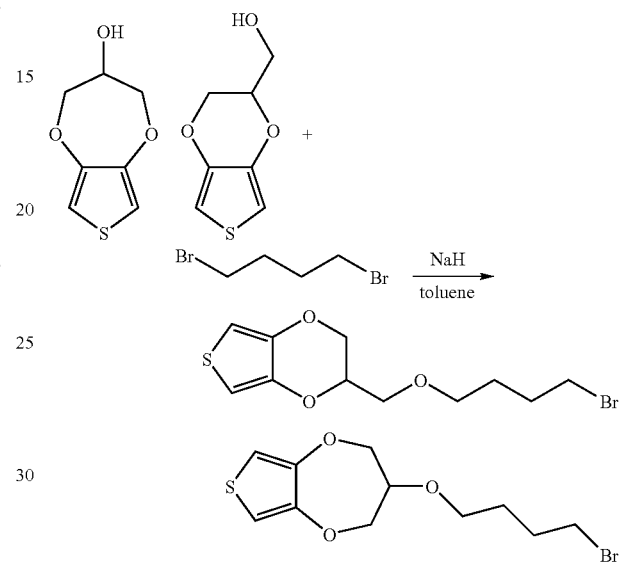

The reaction is carried out under nitrogen 4 g of sodium hydride (60% in mineral oil, 0.1 mol) are washed twice with dry toluene, and then suspended in 100 ml of toluene. This suspension is heated to 80° C. and 10 g of EDT-methanol/hydroxy-PDT (about 80:20, 58.1 mmol, based on the mixture) dissolved in 80 ml of toluene are added dropwise over a period of 35 minutes. The colourless suspension becomes brown. After a further hour, 45 ml (82.35 g=0.381 mol) of 1,4-dibromobutane are added. The solution is stirred at 80° C. for 5 hours, and the heating is then switched off and the solution is stirred at room temperature for a further 12 hours. 8 ml of water are carefully added to stop the reaction. The reaction mixture is washed twice with 90 ml each time of 1N HCl. The toluene phase is washed again with 180 ml of 1N HCl. The collected HCl phases are extracted three times with 90 ml of chloroform. The collected chloroform phases are discarded and the HCl phase is extracted three times with 50 ml of toluene. The HCl phase is then discarded. The collected toluene phases are washed three times with 120 ml each time of saturated aqueous NaCl solution. The toluene phase is dried over MgSO$_4$, the desiccant is filtered off and the solvent is removed on a rotary evaporator. The excess 1,4-dibromobutane is distilled off at 60° C. in an oil pump vacuum. The crude product is purified by column chromatography (eluant: ethyl acetate/hexane 1:4).

Yield: 8.15 g (26.5 mmol=45.7% of theory) of greenish brown liquid having a content of PDT derivative of 12%

IR ν$^{-1}$ [cm$^{-1}$]=3110 2938, 2918, 2868; 1482, 1452, 1427, 1374, 1247, 1184, 1123, 1019, 856, 758

$^1$H-NMR (500 MHz, CDCl$_3$): δ [ppm]=6.47 (s, 12% 2H); 6.34, 6.33 (2*d, each 88% 1H, $^4$J$_{CH-CH}$: 3.78 Hz); 4.37-4.27 (m, 93% 1H); 4.23 (dd, 88% 1H, J$_{CH-CH}$: 11.66 Hz, with superimposition); 4.10 (dd, 12% 4H); 4.05 (dd, 1H, $J_{CH-CH}$: 11.66 Hz); 3.88-3.80 (m, 12% 1H); 3.69 (dd, 88% 1H, $J_{CH-CH}$: 10.40 Hz); 3.60 (dd, 88% 1H, $J_{CH-CH}$: 10.40 Hz); 3.59 (t, 7% 1H); 3.54 (t, 88% 2H); 3.44 (t, 2H); 2.07-1.64 (2*m, each 2H)

$^{13}$C-NMR (125.75 MHz, CDCl$_3$): δ [ppm]=149.46; 141.92, 141.86; 105.74; 100.11, 99.03; 78.34; 71.92, 69.15; 72.99, 71.30, 69.58, 66.52; 34.00; 29.89, 28.51; 28.88

Elemental Analysis:

|  |  |  |  |
|---|---|---|---|
| calculated: | 43.01% C | 4.92% H | |
| found: | 43.11% C | 4.88% H | |
| MS (EI, 70 eV): m/e = | 306 | M$^+$ | 27.6% |
|  | 227 | C$_{11}$H$_{15}$O$_3$S$^+$ | 25.4% |
|  | 156 | C$_7$H$_7$O$_2$S$^+$ | 21.3% |
|  | 135 | C$_4$H$_8$Br$^+$ | 40.2% | b) Reaction of the Product Mixture from a) with Methyl 4-hydroxybenzoate (Reactant Containing the Group M)

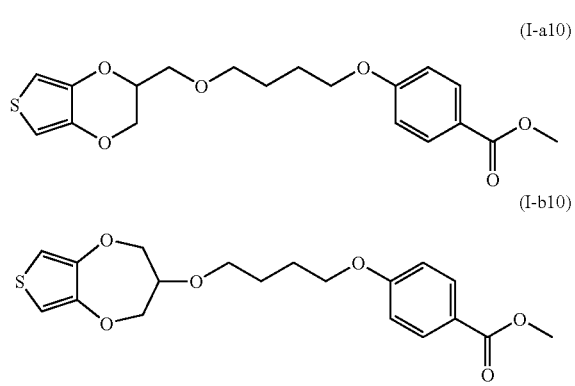

(I-a10)

(I-b10)

0.54 g (3.55 mmol) of methyl 4-hydroxybenzoate, 1.23 g (4.00 mmol) of the product mixture from a) (88% of EDT derivative, 12% of PDT derivative) and 3.39 g (10.4 mmol) of Cs$_2$CO$_3$ are suspended in 30 ml of DMF and stirred at room temperature for 4 days. The work-up is carried out by a method analogous to Example 14b). The crude product is purified by column chromatography (eluant: hexane/ethyl acetate 4:1). This gives a yellowish, viscous oil.

Yield: 1.15 g (3.04 mmol=85.6% of theory) of (I-a10) having a content of PDT derivative of 16%

IR ν$^{-1}$ [cm$^{-1}$]=3111, 2948, 2872; 1711; 1604, 1578, 1483

$^1$H-NMR (500 MHz, CDCl$_3$): δ [ppm]=7.97 (d, 2H, 14-H); 6.89 (d, 2H, 13-H); 6.47 (s, 16% 2H, A-H); 6.32 (s, 84% 2H, 1-H, 2-H); 4.39-4.26 (m, 84% 1H, 6-H); 4.23 (dd, 84% 1H, 5a-H superimposed on dd of Ca—H); 4.12 (dd, 16% 2H, Cb-H); 4.05 (dd, 84% 1H, 5b-H superimposed on 11-H); 4.03 (t, 2H, 11-H superimposed on 5b-H); 3.88 (s, 3H, 17-H); 3.70 (dd, 84% 1H, 7a-H); 3.62 (dd, 84% 1H, 7b-H); 3.57 (t, 84% 2H, 8-H); 1.98-1.84, 1.84-1.69 (2*m, each 2H, 9-H, 10-H)

$^{13}$C-NMR (125.75 MHz, CDCl$_3$): δ [ppm] 165.84; 161.73; 140.51, 140.48; 130.55; 141.41; 113.00; 98.68, 98.59; 71.60, 70.52; 68.16, 66.71, 65.11; 50.82; 25.11, 24.87

Phase Transitions (Determined Using a Polarization Microscope):
C 40.8° C. LC 48.7° C. I (1st heating, <1° C./min)

Phase Transitions (Determined by DSC):

1st heating: onset: 39.57° C., maximum: 44.88° C., endset: 50.06° C.

Elemental Analysis:

|  |  |  |  |
|---|---|---|---|
| calculated: | 60.00% C | 5.86% H | |
| found: | 60.20% C | 6.01% H | |
| MS (EI, 70 eV): m/e = | 378 | M$^+$ | 16.5% |
|  | 227 | C$_{11}$H$_{15}$O$_3$S$^+$ | 26.0% |
|  | 155 | C$_7$H$_7$O$_2$S$^+$ | 32.1% |

Example 17

Cationic, Highly Conductive Polythiophene from (I-a10) and (I-b10) as Coating by In-Situ Polymerization 0.165 g of the thiophene prepared as described in Example 16 (I-a10)/(I-b10) (molar ratio=84:16) is dissolved in 6.625 g of warm n-butanol. 1.562 g of a 40% solution of iron(III) tosylate in n-butanol (Baytron® CB 40; manufacturer: H. C. Starck GmbH) are added quickly to the solution and the mixture is applied by doctor blade coating to a glass plate which has been preheated to about 80° C. (wet film thickness: 24 μm). After drying at 100° C. for 10 minutes and cooling to room temperature (23° C.), the coating is washed with deionized water and dried by means of a hot air dryer. The surface resistance (two-point method) is measured as 276 Ω/square. The plate is annealed at 150° C. for 30 minutes, and the surface resistance after cooling to 23° C. is measured as 66 Ω/square.

Example 18 a) Reaction of an EDT-Methanol/Hydroxy-PDT Mixture with 1,5-dibromopentane (Reactant Containing the Group B)

The reaction corresponds to Example 12a).

b) Reaction of the Product Mixture from a) with Ethyl 4'-hydroxybiphenyl-4-carboxylate (Reactant Containing the Group M)

(I-a11)

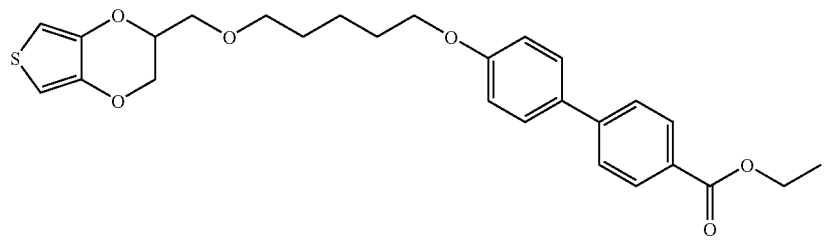

(I-b11)

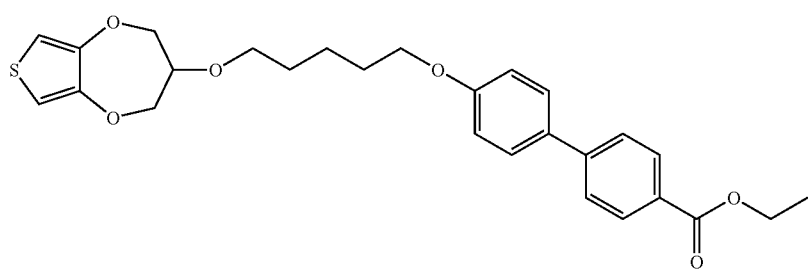

1.08 g (4.46 mmol) of ethyl 4'-hydroxybiphenyl-4-carboxylate, 1.50 g (4.67 mmol) of the product mixture from a) (7% of PDT derivative, 93% of EDT derivative) and 1.55 g (4.76 mmol) of $Cs_2CO_3$ are suspended in 40 ml of DMF and stirred at room temperature for 4 days. The work-up is carried out by a method analogous to Example 12b).

The crude product is recrystallized with methanol/methylene chloride. The colourless precipitate is filtered off, washed with methanol and dried under reduced pressure.

Yield: Fraction 1: 1.08 g (2.24 mmol=50.2% of theory) of (I-a11) in admixture with 3% of PDT derivative (I-b11) Fraction 2: 0.77 g (1.60 mmol=35.8% of theory) of (I-a11) in admixture with 6% of PDT of derivative (I-b11) Fraction 3: 0.18 g (0.37 mmol=8.4% of theory) of (I-a11) in admixture with 30% of PDT derivative (I-b11)

IR $v^{-1}$ [$cm^{-1}$]=2946, 1899, 2869; 1703; 1600, 1581, 1489; 826

$^1$H-NMR (500 MHz, $CDCl_3$): δ [ppm]=8.08 (d, 2H); 7.61 (d, 2H); 7.56 (d, 2H); 6.97 (d, 2H); 6.47 (s, 3% 2H); 6.33, 6.32 (2*d, each 97% 1H); 4.39 (q, 2H), 4.35-4.27 (m, 97% 1H); 4.24 (dd, 1H, $J_{CH-CH}$: 11.66 Hz superimposed dd); 4.11 (dd, 3% 2H), 4.06 (dd, 1H, $J_{CH-CH}$: 11.66 Hz); 4.01 (t, 2H); 3.69 (dd, 1H, $J_{CH-CH}$: 10.40 Hz); 3.61 (dd, 1H, $J_{CH-CH}$: 10.40 Hz); 3.54 (t, 2H); 1.87-1.79, 1.73-1.63, 1.59-1.51 (3*m, each 2H); 1.41 (t, 3H)

$^{13}$C-NMR (125.75 MHZ, $CDCl_3$): δ [ppm]=167.00; 159.68; 145.52; 141.97, 141.93; 132.70; 130.44, 128.73, 126.79; 128.94; 115.29; 100.09, 99.98; 73.04, 72.19; 69.58, 68.25, 66.61; 61.29; 29.68, 29.42; 23.08; 14.78

Phase Transitions (Determined Using a Polarization Microscope):

C 87.7° C. LC 91.6° C. I (1st heating, <1° C./min)

C 87.8° C. LC 94.0° C. I (2nd heating, <1° C./min); LC as early as 70.8° C., but recrystallizes after heating Phase Transitions (Determined by DSC)

1st heating: onset: 84.45° C., maximum: 86.63° C., endset: 90.08° C., heating rate: 110° C./min Elemental Analysis:

| | | | |
|---|---|---|---|
| calculated: | 67.20% C | | 6.27% H |
| found: | 67.28% C | | 6.23% H |
| MS (EI, 70 eV): m/e = | 482 | $M^+$ | 68.5% |
| | 241 | $C_{12}H_{17}O_3S^+$ | 67.5% |
| | 155 | $C_7H_7O_2S^+$ | 40.6% |

Example 19

Cationic, Highly Conductive Polythiophene from (I-a11) and (I-b11) as Coating by In-Situ Polymerization 0.2111 g of the thiophene prepared as described in Example 18 (I-a11)/(I-b11) (fraction 1, molar ratio=97:3) is dissolved in 6.625 g of n-butanol. 1.562 g of a 40% solution of iron(III) tosylate in n-butanol (Baytron®CB 40; manufacturer: H. C. Starck GmbH) are quickly added to the solution and the mixture is applied by doctor blade coating to a glass plate which has been preheated to about 80° C. (wet film thickness: 24 μm). After drying at 80° C. for 10 minutes and cooling to room temperature (23° C.), the coating is washed with deionized water and dried by means of a hot air dryer. The surface resistance (two-point method) is measured as 170 Ω/square. The plate was annealed at 150° C. for 30 minutes, and the surface resistance after cooling to 23° C. is measured as 58 Ω/square.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A 3,4-Alkylenedioxythiophene of the formula (I),

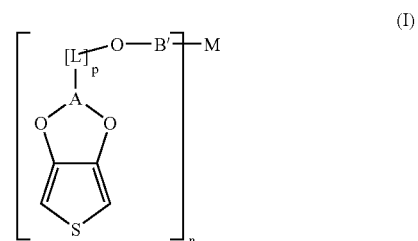

(I)

wherein

A is a $C_1$ or $C_3$-$C_5$-alkylene radical which is substituted at any point by a linker L and optionally bears further substituents, L is a methylene group, p is an integer from 1 to 6, M is an n-functional group of the formula (II-a), (II-b) or (II-c-1) to (II-c-6),

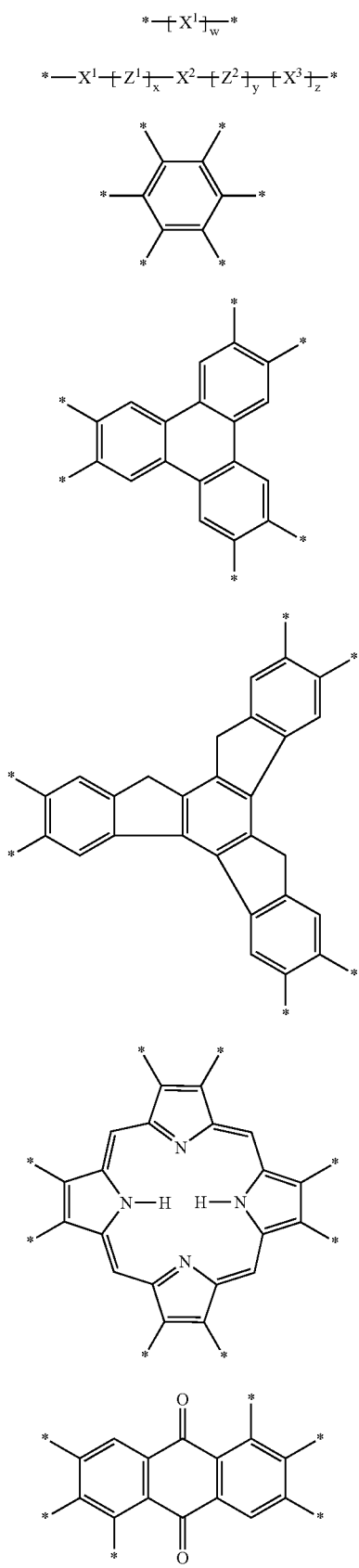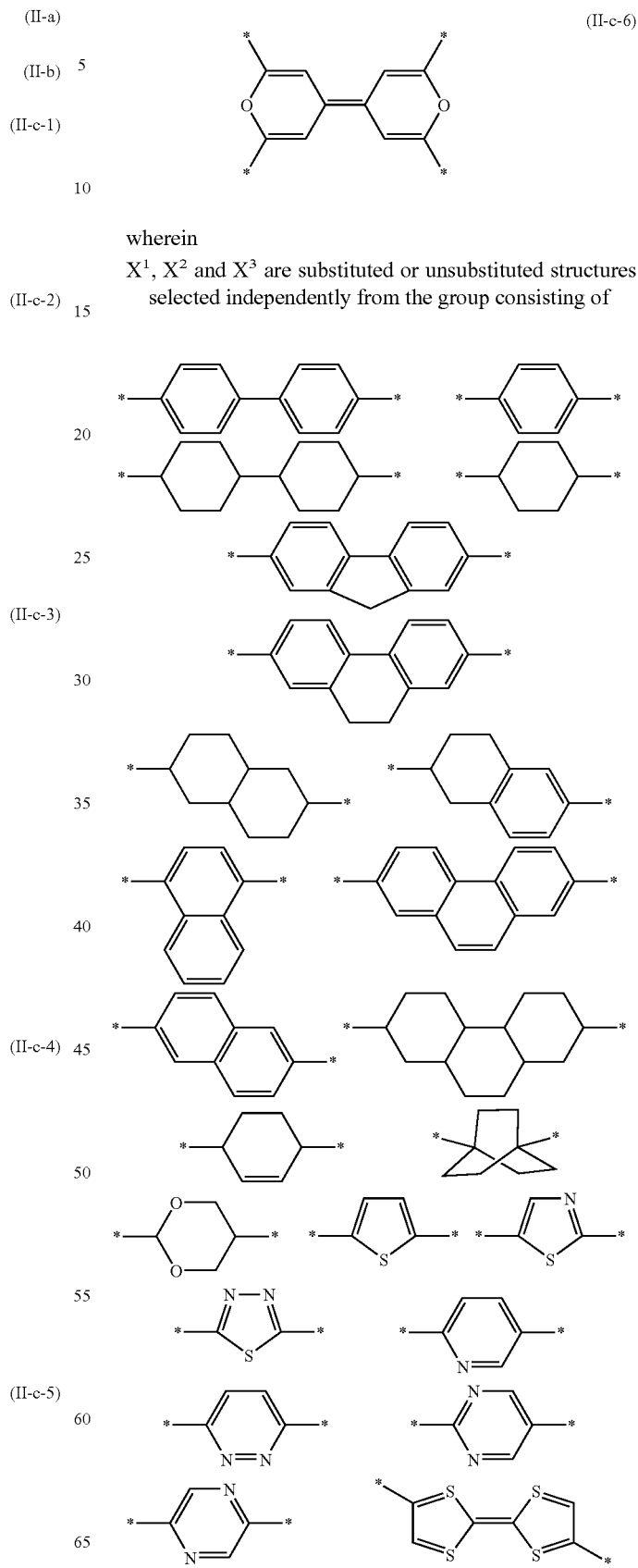
wherein
X¹, X² and X³ are substituted or unsubstituted structures selected independently from the group consisting of -continued

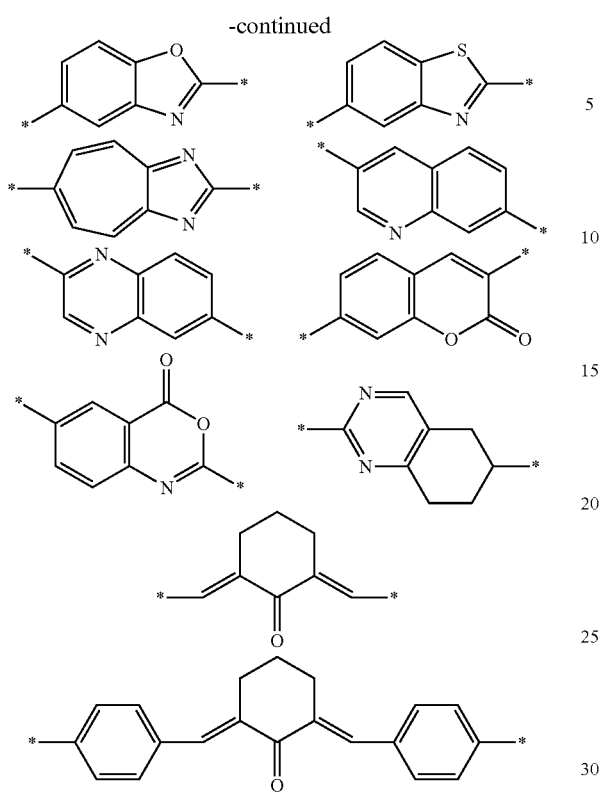

and

Z¹ and Z² are structures selected independently from the group consisting of

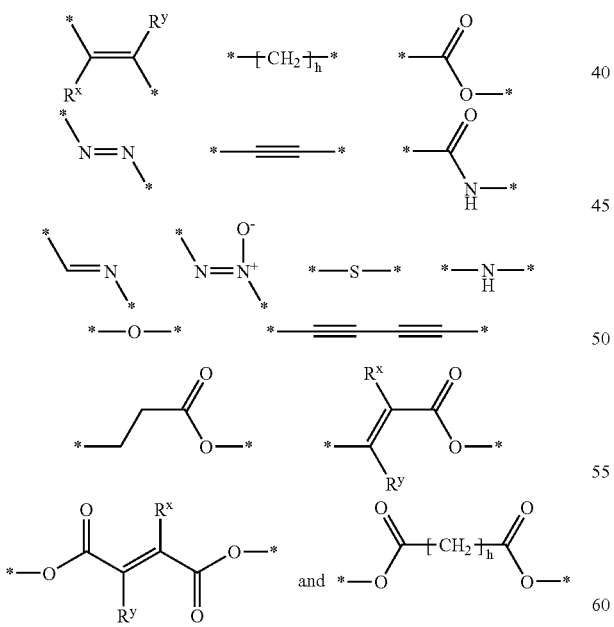

wherein

R$^x$ and R$^y$ are each, independently of one another, H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, $NO_2$, a carboxyl group or a hydroxy group, h is an integer from 1 to 10, w is an integer from 1 to 5, x, y and z are each, independently of one another, 0 or 1, and n an integer from 1 to 8, where when n is an integer below 8, the group is selected from the group consisting of formulas (II-c-1), (II-c-2), (II-c-3), (II-c-4), (II-c-5) and (II-c-6) and bears a terminal group F' on the remaining 8-n linkage points denoted by * when n is 1, the group of the formula (II-a) or (II-b) and bears a terminal group F' at the linkage points denoted by *, wherein F' is H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, a nitro ($NO_2$) group, a carboxyl group, a sulphonic acid group or sulphonate group or a hydroxy group, B' is a bridging group of the formula (B)

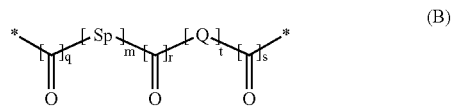

(B)

wherein q is 0 or 1, r and s are identical or different and each are 0 or 1, with the proviso that when r is 1, s is 0 and vice versa or both are optionally 0, t is 0 or 1, Sp is a spacer selected from the group consisting of substituted and unsubstituted linear or cyclic $C_1$-$C_{20}$-alkylene groups, $C_5$-$C_{20}$-arylene groups, $C_2$-$C_{20}$-heteroarylene groups in which from one to three heteroatoms selected from the group consisting of N, O and S can additionally be present in the heteroaromatic ring or ring system, $C_6$-$C_{20}$-aralkylene groups, $C_2$-$C_{200}$-oligoether and polyether groups, m is 0 or 1, and Q is O, S or NH.

2. The 3,4-Alkylenedioxythiophene of claim 1, wherein

M is an n-functional group selected from the group consisting of the formulae (II-c-1) to (II-c-6),

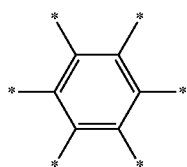

(II-c-1)

-continued

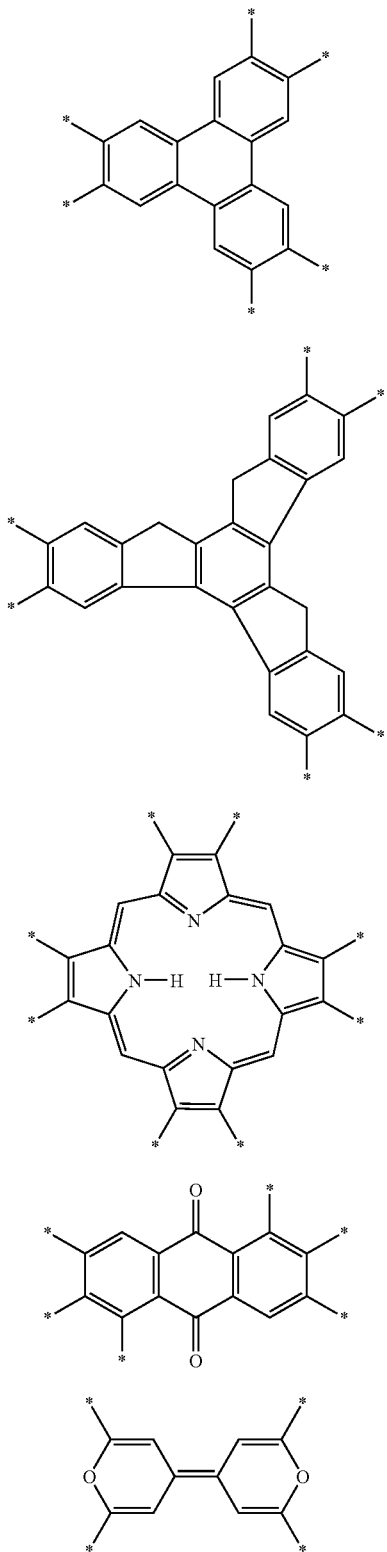

wherein
n is at most 4, 6 or 8,
and wherein when n is an integer below 4, 6 or 8, M is selected from the group consisting of the formulae (II-c-1) to (II-c-6) bearing a terminal group F' on the remaining 4-n, 6-n or 8-n linkage points denoted by *,
wherein
F' is H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, a nitro ($NO_2$) group, a carboxyl group, a sulphonic acid group or sulphonic group or a hydroxy group.

3. The 3,4-Alkylenedioxythiophene of claim 1, having the structure of the formula (I-b),

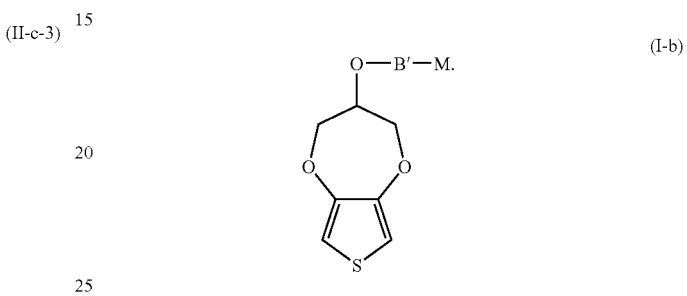

4. A 3,4-Alkylenedioxythiophene of the formula (I),

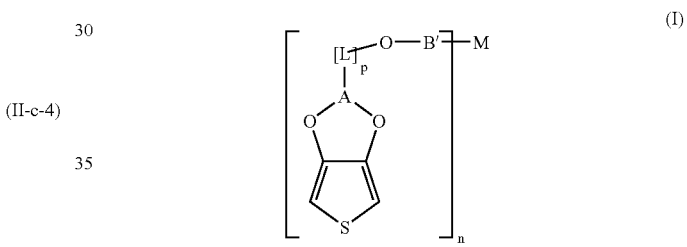

wherein
A is a $C_1$-$C_5$-alkylene radical which is substituted at any point by a linker L and optionally bears further substituents,
L is a methylene group,
p is 0 or an integer from 1 to 6,
M is an n-functional steroid radical or a derivative of a steroid radical,
n island
B' is a bridging group of the formula (B)

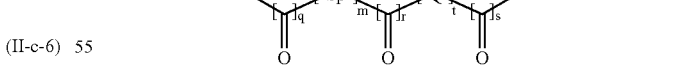

wherein
q is 0 or 1,
r and s are each independently 0 or 1, with the proviso that when r is 1, s is 0 and vice versa or both are optionally 0,
t is 0 or 1,
Sp is a spacer selected from the group consisting of substituted and unsubstituted linear or cyclic $C_1$-$C_{20}$-alkylene groups, $C_5$-$C_{20}$-arylene groups, $C_2$-$C_{20}$-heteroarylene groups in which from one to three heteroatoms selected from the group consisting of N, O and S can additionally be present in the heteroaromatic ring or ring system, $C_6$-$C_{20}$-aralkylene groups, $C_2$-$C_{200}$-oligoether and -polyether groups, m is 0 or 1, Q is O, S or NH.

5. The 3,4-Alkylenedioxythiophene as claimed in claim 4, wherein

M is an n-functional cholesteryl radical or a derivative of the cholesteryl radical of the formula (III-a)-(III-e),

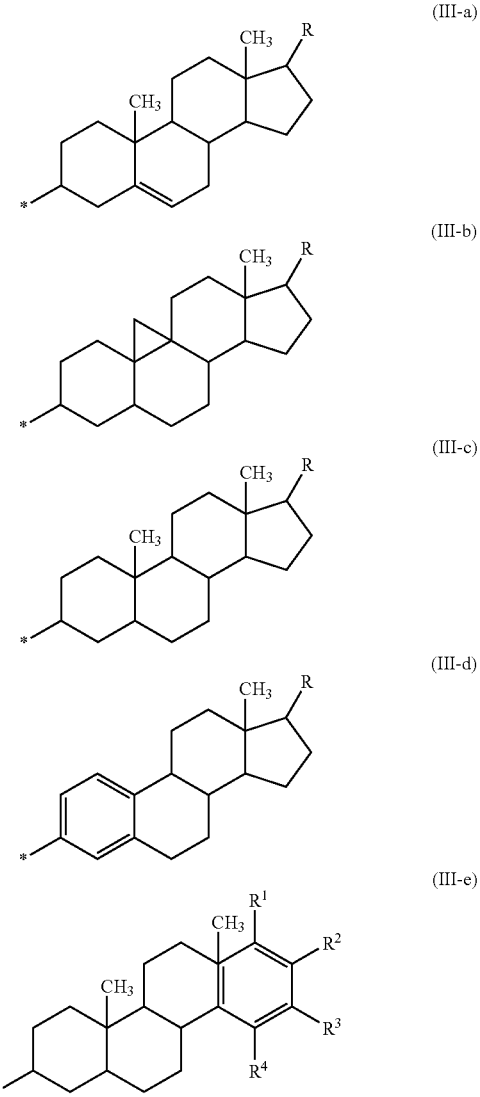

wherein R is H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_2$-alkanecarboxylic acid or of acrylic acid, halogen, pseudohalogen, a nitro ($NO_2$) group, a carboxyl group, a sulphonic acid group or sulphonic group or a hydroxy group, and $R^1$, $R^2$, $R^3$ and $R^4$ can, independently of one another, be as defined above for R.

6. A process for preparing a polythiophene comprising polymerizing the 3,4-alkylenedioxythiophene as claimed in claim 1.

7. A process for preparing a polythiophene comprising mixing two or more of the 3,4-Alkylenedioxythiophene as claimed in claim 1 to form a mixture and polymerizing the mixture.

8. A process for preparing electrical or electronic components, light-emitting components, for antistatic coating, in optoelectronics or in solar energy technology comprising incorporating the 3,4-alkylenedioxythiophene according to claim 1.

9. The process according to claim 7, wherein the polymerized mixture forms a layer which further comprises heating the layer at a temperature form 80° C. to 300° C.

10. A process for preparing the polythiophene, comprising oxidatively polymerizing electro chemically the 3,4-alkylenedioxythiophene according to claim 1.

11. A 3,4-Alkylenedioxythiophene of the formula (I),

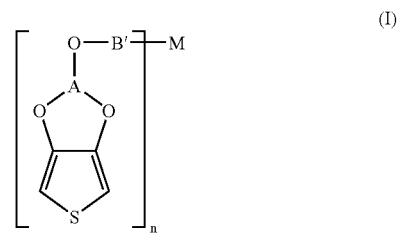

wherein

A is a $C_1$-$C_5$-alkylene radical which is substituted at any point by a linker L and optionally bears further substituents, M is an n-functional group of the formula (II-a), (II-b) or (II-c-1) to (II-c-6),

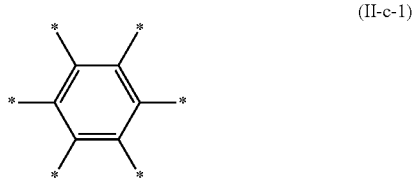

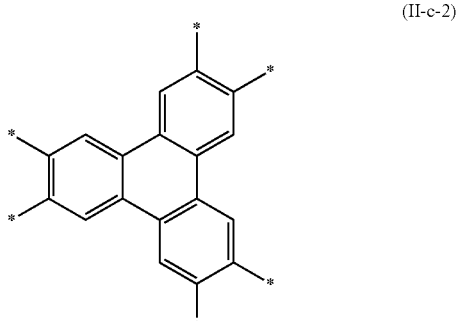

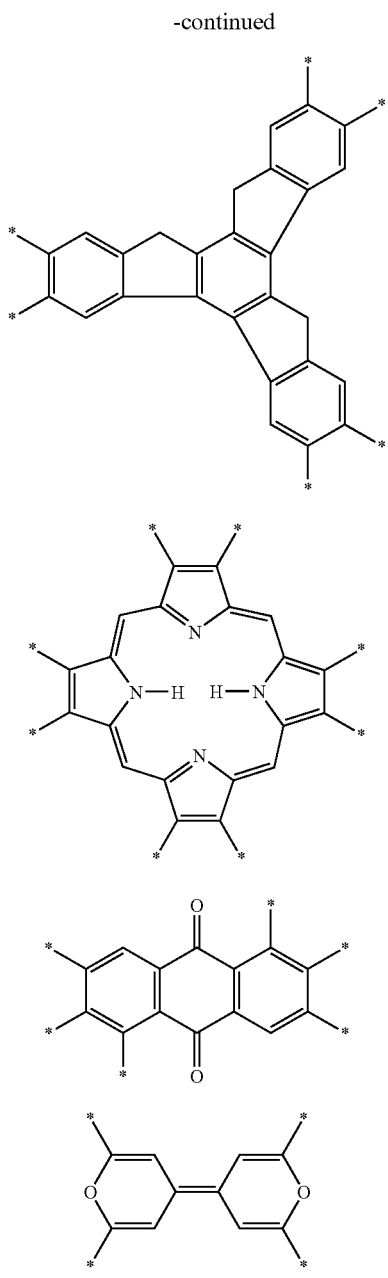
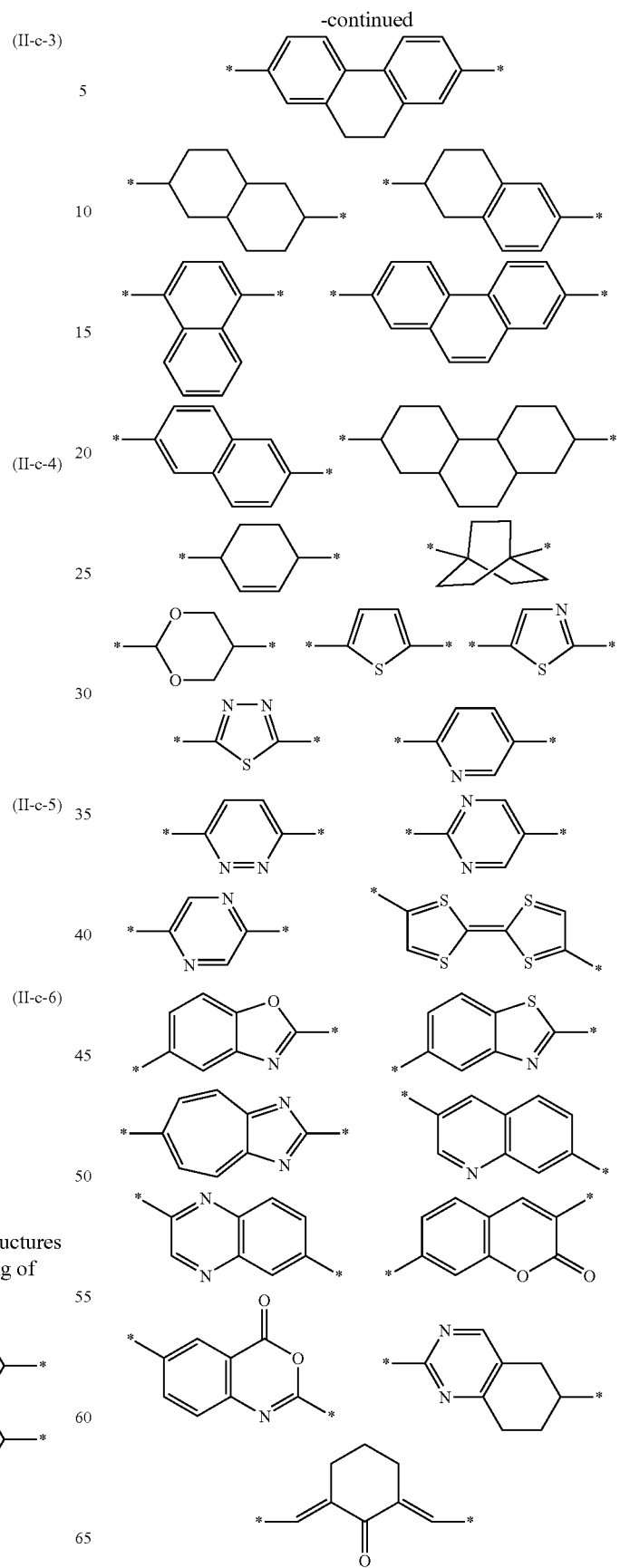
wherein
$X^3$, $X^2$ and $X^3$ are substituted or unsubstituted structures selected independently from the group consisting of
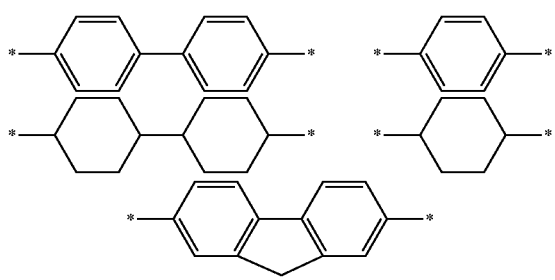

-continued

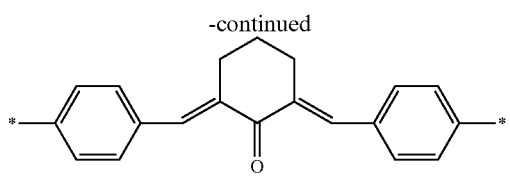

and
$Z^1$ and $Z^2$ are structures selected independently from the group consisting of

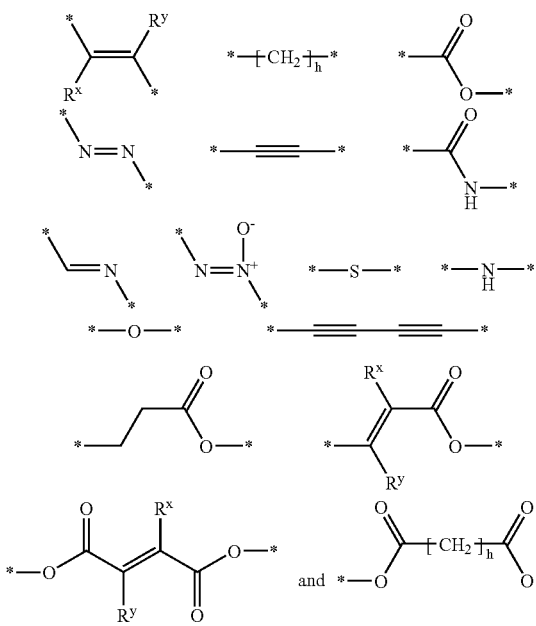

wherein
$R^x$ and $R^y$ are each, independently of one another, H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, $NO_2$, a carboxyl group or a hydroxy group, h is an integer from 1 to 10,
w is an integer from 1 to 5,
x, y and z are each, independently of one another, 0 or 1, and
n an integer from 1 to 8, where when n is an integer below 8, the group is selected from the group consisting of formulas (II-c-1), (II-c-2), (II-c-3), (II-c-4), (II-c-5) and (II-c-6) and bears a terminal group F' on the remaining 8-n linkage points denoted by * when n is 1, the group of the formula (II-a) or (II-b) and bears a terminal group F' at the linkage points denoted by *,
wherein
F' is substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, a nitro ($NO_2$) group, a carboxyl group, a sulphonic acid group or sulphonate group or a hydroxy group, B' is a bridging group of the formula (B)

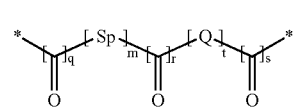

wherein
q is 0 or 1,
r and s are identical or different and each are 0 or 1, with the proviso that when r is 1, s is 0 and vice versa or both are optionally 0,
t is 0 or 1,
Sp is a spacer selected from the group consisting of substituted and unsubstituted linear or cyclic $C_1$-$C_{20}$-alkylene groups, $C_5$-$C_{20}$-arylene groups, $C_2$-$C_{20}$-heteroarylene groups in which from one to three heteroatoms selected from the group consisting of N, O and S can additionally be present in the heteroaromatic ring or ring system, $C_6$-$C_{20}$-aralkylene groups, $C_2$-$C_{200}$-oligoether and polyether groups,
m is 0 or 1, and
Q is QS or NH.

12. A 3,4-Alkylenedioxythiophene of the formula (I),

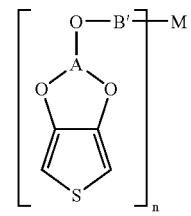

wherein
A is a $C_1$-$C_5$-alkylene radical which is substituted at any point by a linker L and optionally bears further substituents,
M is an n-functional group of the formula (II-a), (II-b) or (II-c-1) to (II-c-6),

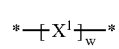

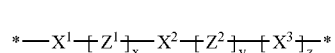

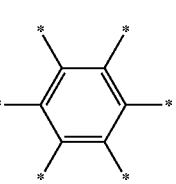

-continued
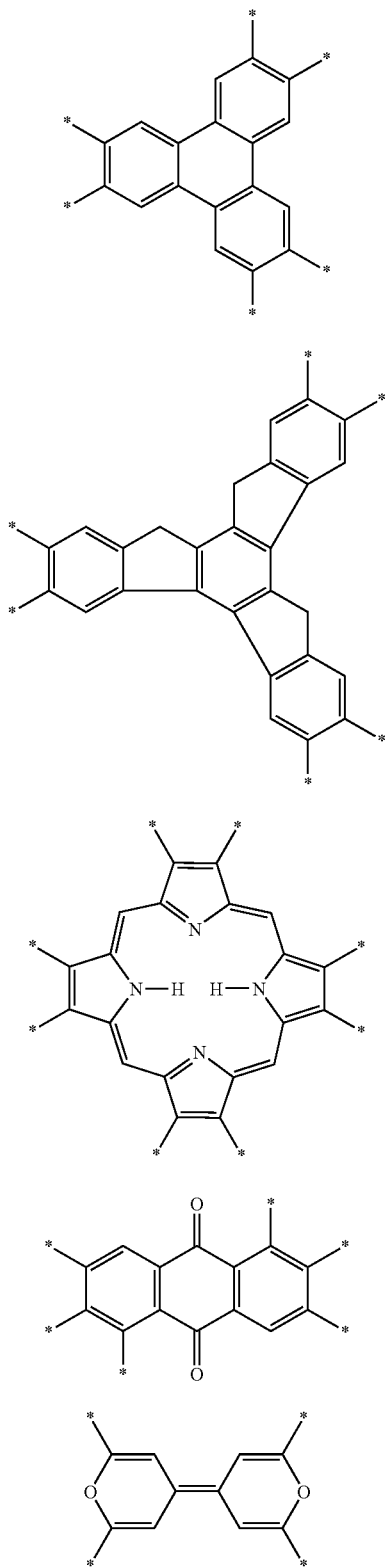
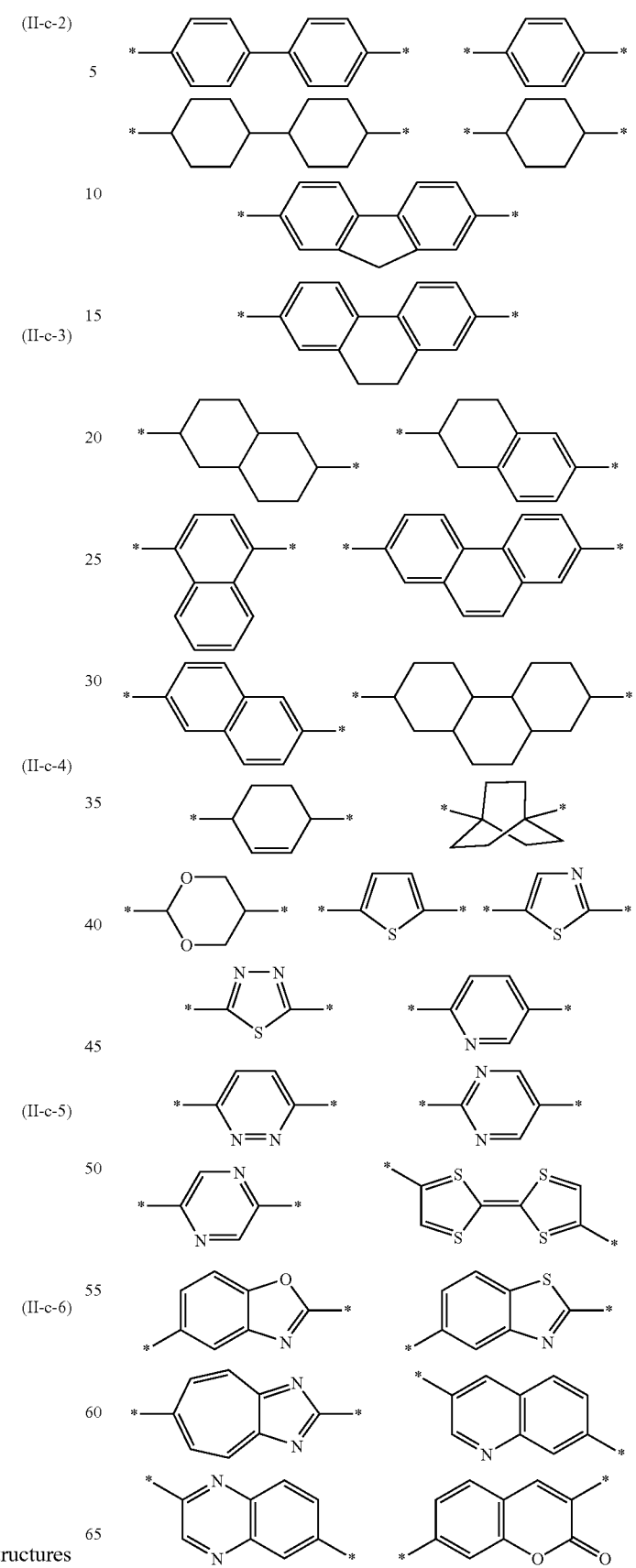
wherein
X[1], X[2] and X[3] are substituted or unsubstituted structures selected independently from the group consisting of -continued

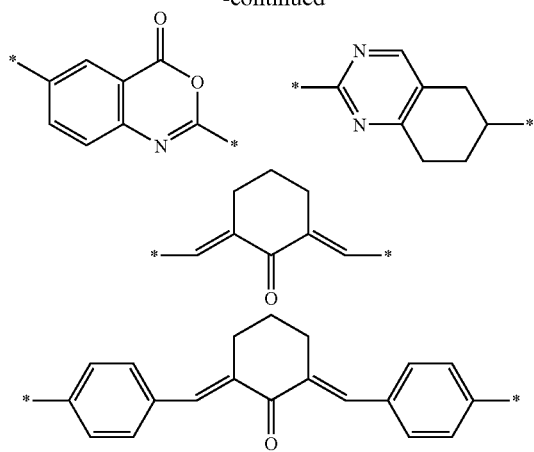

and
$Z^1$ and $Z^2$ are structures selected independently from the group consisting of

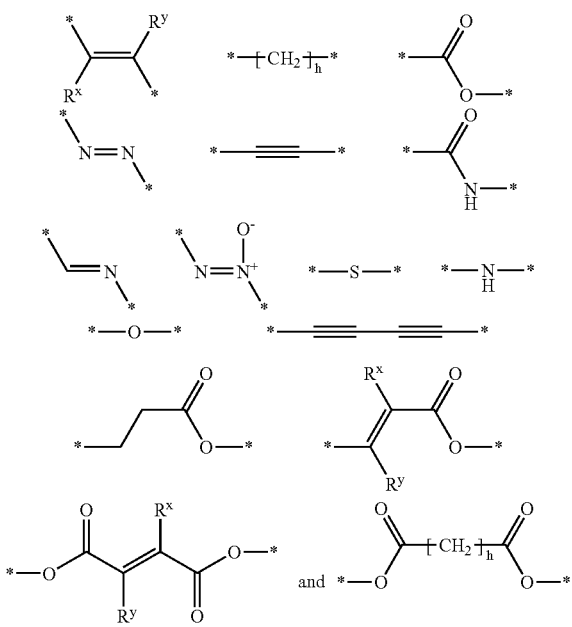

wherein
$R^x$ and $R^y$ are each, independently of one another, H, substituted or unsubstituted $C_1$-$C_{22}$-alkyl, $C_1$-$C_{22}$-haloalkyl, $C_3$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, $NO_2$, a carboxyl group or a hydroxy group, h is an integer from 1 to 10,
w is an integer from 1 to 5,
x, y and z are each, independently of one another, 0 or 1, and
n an integer from 1 to 8, where when n is an integer below 8, the group is selected from the group consisting of formulas (II-c-1), (II-c-2), (II-c-3), (II-c-4), (II-c-5) and (II-c-6) and bears a terminal group F' on the remaining 8-n linkage points denoted by * when n is 1, the group of the formula (II-a) or (II-b) and bears a terminal group F' at the linkage points denoted by *, wherein
F' is H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, a nitro ($NO_2$) group, a carboxyl group, a sulphonic acid group or sulphonic group or a hydroxy groups B' is a bridging group of the formula (B)

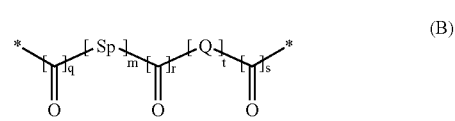

(B)

wherein
q is 0 or 1,
r is 1,
s is 0,
t is 0 or 1,
Sp is a spacer selected from the group consisting of substituted and unsubstituted linear or cyclic $C_1$-$C_{20}$-alkylene groups, $C_5$-$C_{20}$-arylene groups, $C_2$-$C_{20}$-heteroarylene groups in which from one to three heteroatoms selected from the group consisting of N, O and S can additionally be present in the heteroaromatic ring or ring system, $C_6$-$C_{20}$-aralkylene groups, $C_2$-$C_{200}$-oligoether and polyether groups,
m is 0 or 1, and
Q is O, S or NH.

13. A polythiophene which comprise recurring units of the formula (IV),

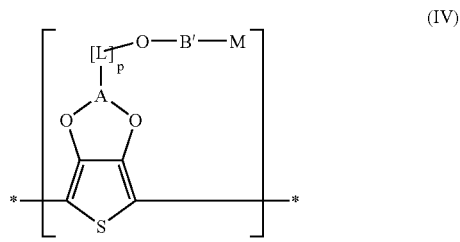

(IV)

wherein
A is a $C_1$ or $C_3$-$C_5$-alkylene radical which is substituted at any point by a linker L and optionally bears further substituents,
L is a methylene group,
p is an integer from 1 to 6,
M is an n-functional group of the formula (II-a), (II-b) or (II-c-1) to (II-c-6),

(II-a)

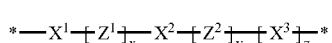

(II-b)

-continued (II-c-1)
(II-c-2)
(II-c-3)
(II-c-4)
(II-c-5)

-continued (II-c-6)

wherein
X$^1$, X$^2$ and X$^3$ are substituted or unsubstituted structures selected independently from the group consisting of -continued

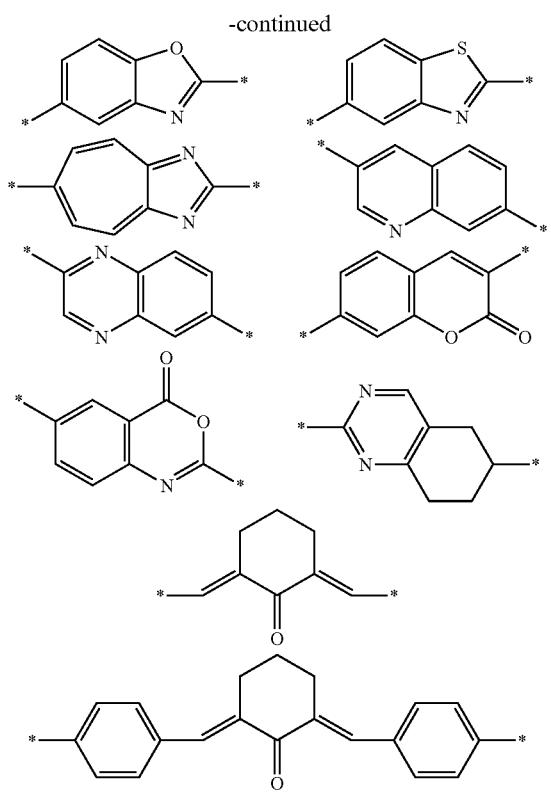

and
$Z^1$ and $Z^2$ are structures selected independently from the group consisting of

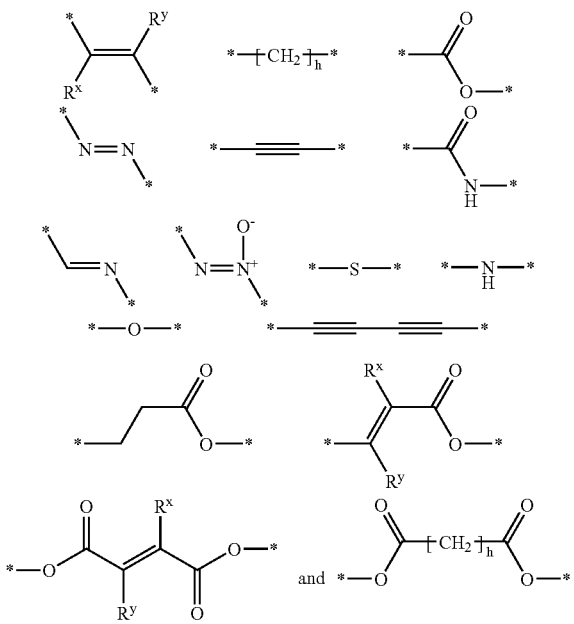

wherein
$R^x$ and $R^y$ are each, independently of one another, H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, $NO_2$, a carboxyl group or a hydroxy group, h is an integer from 1 to 10, w is an integer from 1 to 5, x, y and z are each, independently of one another, 0 or 1, and n an integer from 1 to 8, where when n is an integer below 8, the group is selected from the group consisting of formulas (II-c-1), (II-c-2), (II-c-3), (II-c-4), (II-c-5) and (II-c-6) and bears a terminal group F' on the remaining 8-n linkage points denoted by * when n is 1, the group of the formula (II-a) or (II-b) and bears a terminal group F' at the linkage points denoted by *, wherein F' is H, substituted or unsubstituted $C_1$-$C_{22}$-alkyl, $C_1$-$C_{22}$-haloalkyl, $C_1$-$C_{22}$-alkenyl, $C_1$-$C_{22}$-alkoxy, $C_1$-$C_{22}$-thioalkyl, $C_1$-$C_{22}$-iminoalkyl, $C_1$-$C_{22}$-alkoxycarbonyl, $C_1$-$C_{22}$-alkoxycarbonyloxy, a radical of an aliphatic $C_1$-$C_{22}$-alkanecarboxylic acid or of acrylic acid, halogen, pseudohalogen, a nitro ($NO_2$) group, a carboxyl group, a sulphonic acid group or sulphonic group or a hydroxy group, B' is a bridging group of the formula (B)

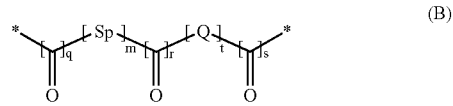

(B)

wherein q is 0 or 1, r and s are identical or different and each are 0 or 1, with the proviso that when r is 1, s is 0 and vice versa or both are optionally 0, t is 0 or 1, Sp is a spacer selected from the group consisting of substituted and unsubstituted linear or cyclic $C_1$-$C_{20}$-alkylene groups, $C_5$-$C_{20}$-arylene groups, $C_2$-$C_{20}$-heteroarylene groups in which from one to three heteroatoms selected from the group consisting of N, O and S can additionally be present in the heteroaromatic ring or ring system, $C_6$-$C_{20}$-aralkylene groups, $C_2$-$C_{200}$-oligoether and polyether groups, m is 0 or 1, and Q is O, S or NH.

14. A process for preparing electrical or electronic components, light-emitting components, for antistatic coating, in optoelectronics or in solar energy technology comprising incorporating the polythiophene of claim 13.

15. A process for preparing conductive layers comprising incorporating the polythiophene according to claim 13.

16. The process according to claim 15, which further comprises heating the layer at a temperature form 80° C. to 300° C.

17. The polythiophene of claim 13, wherein they are cationically and electrically conductive and contain bound anions as counterions to balance the positive charge.

18. The polythiophene of claim 17, wherein the counterions are polyanions of polymeric carboxylic acids or polymeric sulphonic acids.

19. The polythiophene according to claim 13, wherein they are uncharged and semiconducting.

* * * * *

UNITED STATES PATENT AND TRADEMARK OFFICE
CERTIFICATE OF CORRECTION

PATENT NO. : 7,585,983 B2
APPLICATION NO. : 10/762106
DATED : September 8, 2009
INVENTOR(S) : Knud Reuter et al.

It is certified that error appears in the above-identified patent and that said Letters Patent is hereby corrected as shown below:

In the Claims:

In Claim 4, column 46, line 49, "n island" should be deleted and insert -- n is 1 and --.

In Claim 10, column 48, line 16, "electro chemically" should be deleted and insert -- electrochemically --.

Signed and Sealed this

Tenth Day of November, 2009

David J. Kappos
*Director of the United States Patent and Trademark Office*